(12) United States Patent
Moores et al.

(10) Patent No.: US 8,329,617 B2
(45) Date of Patent: Dec. 11, 2012

(54) COMPOSITIONS AND METHODS FOR SYNERGISTIC MANIPULATION OF PLANT AND INSECT DEFENSES

(75) Inventors: Graham Moores, Harpenden (GB); Georgina Bingham, Harpenden (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 12/774,414

(22) Filed: May 5, 2010

(65) Prior Publication Data

US 2010/0267677 A1 Oct. 21, 2010

Related U.S. Application Data

(63) Continuation of application No. PCT/GB2008/001419, filed on Apr. 24, 2008.

(30) Foreign Application Priority Data

Nov. 6, 2007 (GB) .................................. 0721761.5

(51) Int. Cl.
*A01N 25/26* (2006.01)
(52) U.S. Cl. ........................................................ 504/100
(58) Field of Classification Search ................... 504/100, 504/117
See application file for complete search history.

(56) References Cited

U.S. PATENT DOCUMENTS

| | | | |
|---|---|---|---|
| 5,153,182 A | 10/1992 | Tozzi | |
| 6,890,525 B2 | 5/2005 | Hick et al. | |
| 6,986,898 B1 * | 1/2006 | Bessette | 424/406 |
| 2005/0147635 A1 * | 7/2005 | Hick et al. | 424/405 |
| 2007/0042182 A1 * | 2/2007 | Markus et al. | 428/402.2 |

FOREIGN PATENT DOCUMENTS

| | | |
|---|---|---|
| EP | 0713647 A1 * | 5/1996 |
| EP | 0779030 A1 | 6/1997 |
| EP | 1235483 A2 | 9/2002 |
| EP | 1499183 A1 | 1/2005 |
| EP | 1715739 A2 | 11/2006 |
| EP | 1742728 A1 | 1/2007 |
| WO | 0100026 A1 | 1/2001 |
| WO | WO 0100026 A1 * | 1/2001 |
| WO | 0141568 A2 | 6/2001 |
| WO | 03051120 A1 | 6/2003 |
| WO | 03092378 A1 | 11/2003 |
| WO | 2004052101 A1 | 6/2004 |
| WO | 2005094580 A1 | 10/2005 |
| WO | 2006100308 A2 | 9/2006 |
| WO | 2006111553 A1 | 10/2006 |
| WO | 2006111570 A2 | 10/2006 |
| WO | 2008094562 A2 | 8/2008 |
| WO | 2008151781 A2 | 12/2008 |

OTHER PUBLICATIONS

James, Further Field Evaluation of SYnthetic Herbivore-induced Plant Volatiles as Attractants for Beneficial Insects, J. Chem. Ecology 31: 481-495 (2005).*
Birkett et al., New Roles for cis-Jasmone as an Insect Semiochemical and in Plant Defense, Proc. Natl. Acad. Sci. USA 97: 9329-9334 (2000).*
Birkett et al., Proc Natl Acad Sci USA 97: 9329-9324 (2000).*
James, J Chem Ecology 31: 481-495 (2005).*
Baldwin, et al., "Effects of Octadecanoid Metabolites and Inhibitors on Induced Nicotine Accumulation in Nicotiana Sylvestris," Journal of Chemical Ecology, vol. 22, No. 1, 1996.
Gullino, et al., "Uses and Challenges of Novel Compounds for Plant Disease Control," Crop Protection 19(2000) 1-11.
Miles, et al., "Field Evaluation of a Plant Activator, Captan, Chlorothalonil, Copper Hydroxide, Iprodione, Mancozeb and Strobilurins for the Control of Citrus Brown Spot of Mandarin," Australasian Plant Pathology, 2005, 34, 63-71.
International Preliminary Report on Patentability relating to corresponding PCT/GB2008/001419, May 28, 2010.
Written Opinion relating to corresponding PCT/GB2008/001419, May 27, 2009.
International Search Report on Patentability relating to corresponding PCT/GB2008/001419, May 27, 2009.

* cited by examiner

*Primary Examiner* — Robert T Crow
*Assistant Examiner* — Thor Nielsen
(74) *Attorney, Agent, or Firm* — Banner & Witcoff, Ltd.

(57) ABSTRACT

This invention relates to the control of plant pests, such as aphid and whitefly by treating plants with a compound which inhibits the plant pest's ability to overcome plant defense responses, such as piperonyl butoxide or propyl gallate, in combination with a compound which activates plant defense responses, such as cis-Jasmone or beta-amino butyric acid.

22 Claims, 15 Drawing Sheets

COMPOSITIONS AND METHODS FOR SYNERGISTIC MANIPULATION OF PLANT AND INSECT DEFENSES

RELATED APPLICATIONS

This application is a continuation of PCT application number PCT/GB2008/001419 designating the United States and filed Apr. 24, 2010; which claims the benefit of GB patent application number 0721761.5 and filed Nov. 6, 2007 both of which are hereby incorporated by reference in their entireties.

FIELD OF THE INVENTION

This invention relates to compositions and methods for protecting plants from pest infestation.

BACKGROUND OF THE INVENTION

The development of insecticide resistance in a wide range of important insect pest species poses a serious challenge to effective crop protection, creating an urgent need for alternative control strategies. The problem is exemplified in the UK by recent difficulties in controlling aphids and globally by the intensive use of chemicals in attempts to control whitefly.

Pesticide resistance is often due to the enhancement of metabolic enzyme systems within the insect, particularly non-specific esterases and microsomal oxidases. These enzymes are present in insects to enable them to metabolise plant xenobiotics, but selection pressure from pesticides can result in greatly enhanced activity and insecticide resistance. It is known that inhibitors of these enzyme systems (insecticide synergists) can result in increased potency of insecticides. If such synergists are allowed sufficient time to inhibit these enzymes fully (temporal synergism) then the sensitivity of insect pests to pesticides can be increased by several orders of magnitude (Moores et al., 2005; Young et al., 2005; 2006; Bingham et al., 2007).

A number of natural and synthetic compounds induce effective plant resistance (including natural xenobiotics) by acting at specific points in plant defence pathways; BABA (β-amino butyric acid) and cis-jasmone are two examples of such chemicals. BABA, a non-protein amino acid is a potent inducer of resistance to plant pathogens, including viruses, bacteria, fungi and nematodes. Recent research at Imperial College has revealed that BABA also enhances plant resistance to insect pests, including aphids and Lepidoptera. Aphids on BABA-treated plants show very poor growth and survival (Hodge et al., 2005; 2006). Unlike other chemical inducers, BABA does not directly activate the plant's natural defence arsenal and therefore does not impose yield drag on crops. Instead, BABA conditions the plant for a faster and stronger activation of defence responses once attack by pest or pathogen has started, a process known as 'priming'. The broad-spectrum protection conferred by BABA is effective against a wide range of pest and pathogen species, and operates in crop plants from many botanical families, making BABA a compound of enormous potential.

cis-Jasmone is a volatile plant activator involved with plant resistance (Birkett et al., 2000). Its activity was first discovered at Rothamsted Research when components of blackcurrant volatiles that repelled the summer form of lettuce aphid, *Nasonovia ribisnigri*, were being identified. Since then, cis-jasmone has been found to have more intricate effects on interactions between pest insects and crop plants. cis-jasmone may also act as an external signal, alerting recipient plants when their neighbours are being damaged by phytophagous insects and thereby enabling them to prepare their own defences prior to insect attack (Chamberlain et al., 2000, Pickett & Poppy 2001). The practical use of cis-jasmone initially focused on the interaction between the grain aphid *Sitobion avenae* and wheat, *Triticum aestivum*. Wheat plants sprayed with low levels of cis-jasmone as an aqueous emulsion were found to be less attractive to aphids, but more attractive to their parasitoids in laboratory bioassays. In the field, similarly treated plants had lower aphid infestations (Bruce et al., 2003). See also WO01/41568, EP Patent 1235483, and U.S. Pat. No. 6,890,525, herein incorporated by reference.

Examples of crop pests for which various treatments have been attempted include, but are not limited to, *Myzus persicae*, the peach-potato aphid. This is an important polyphagous insect pest of many commercial crops. One such crop is sweet pepper, *Capsicum annuum*, grown under glass, of which *M. persicae* is the most important vector of viral disease. Current control measures include the application of an aphicide or the use of biological control agents, particularly aphid parasitoids. The effect of the plant activator cis-jasmone as a switch to induce expression of defence-related biosynthetic pathways in sweet peppers, so as to reduce aphid colonisation and increase foraging efficiency of aphid parasitoids under glass, has been shown to be effective (Dewhirst, 2007).

*Bemisia tabaci*, the tobacco whitefly, is another globally important insect pest. In particular, the B&Q-biotypes are extremely invasive and resistant to many conventional insecticides. The host range consists of over 500 species in 74 families, covering almost all major agricultural systems, from cotton and vegetable field crops to ornamentals (Gunning et al., 1998). The tobacco whitefly has not been tested with cis-jasmone previously.

WO01/00026 discloses a tripartite composition for pest control comprising (a) a plant essential oil; (b) an enzyme inhibitor and (c) a synergist.

SUMMARY OF THE INVENTION

In light of the development of resistance to insecticides, there is a need in the art for new methods of pest control. This invention addresses this need by providing compositions and methods which employ synergists to reduce pest defences in an appropriate temporal relationship with plant activators which prime plants to produce defensive xenobiotics. These methods and compositions may be used with or without additional toxic compounds, such as insecticides. Since temporal synergism leaves the insect defenceless, the exposure of plants to be protected to the combined actions of appropriate synergists and activators has the potential to enhance the potency of plant activators as well as insecticides. Indeed, with crops that have relatively toxic secondary metabolites (such as legumes, potatoes and brassicas), the use of temporal synergism in conjunction with plant activator priming results in low pest survival even without the use of pesticides. This approach offers substantial advantages in terms of the reduced amounts of insecticide which are required to kill resistant pests, which has benefits in terms of environmental impact and beneficial insects.

Aspects of this invention provide methods and compositions whereby plant defence synergists (for example, PBO (piperonyl butoxide), analogs of PBO, other MDPs (methylenedioxyphenyl) compounds and other pesticide synergists), are contacted with plants before, after or concurrent with appropriate plant activators (e.g. cis-Jasmone, analogs thereof, BABA or other activators). Plant species which may be protected in this way protected from pests (including but not limited to aphids and whitefly) include crops and non-crops, monocots and dicots. In some embodiments, the methodology and compositions described herein may have additional benefits, such as attracting beneficial insect parasites to plants.

Various formulations and compositions described herein provide delayed release and/or timed release of synergist and activator. This reduces the need for separate and repeated applications of active compounds in the field. These include, but are not limited to, use of microencapsulants containing cyclodextrins, yeast, gum acacia, polyurea, or combinations of these for the delayed release of either or both of the synergist or plant activator, either simultaneously or separately. In producing compositions and practicing the methods described herein, those skilled in the art will readily appreciate that known technologies may be appropriately and easily adapted. Thus, for this purpose, reference is made to WO06111553 (polyurea and other multilayer encapsulants); WO06111570 and EP17157392 (cyclodextrin encapsulation), WO06100308 and EP1742728 (for yeast and other microbial cell encapsulation technologies), and U.S. Pat. No. 5,153,182, EP1499183 and WO03092378 (for examples of insecticide synergist combinations), all of which are herein incorporated by reference for purposes of enabling those skilled in the art to utilize the present disclosure to achieve the novel methods of delivery and compositions according to the present invention.

Accordingly, the invention provides, in various aspects, methods and compositions for maximal inhibition of insect pests (e.g. aphid and whitefly) enzymes by providing an appropriate synergist before, after or concurrent with treatment with effective amounts (either as a single or multiple doses) of a plant activator to combat a wide variety of plant pests.

Examples of appropriate synergists include piperonyl butoxide (PBO), an analog thereof, sesamex, sesamolin, sesamin, sulfoxide, tropital, propyl isome, MGK 264, propynyl phosphonate, N-isobutylundecylenamide, octachlorodipropyl ether, another methylenedioxyphenyl, MDP compound, an ester of gallic acid including, but not limited to, propyl-gallate, octyl-gallate, or an unrelated synergist now known or hereinafter developed.

Examples of activators include cis-jasmone, methyl jasmonate, methyl salicylate and salicylic acid, analogues thereof, and BABA.

Other aspects of the invention provide combined and single treatments of synergists, and activators to control specifically aphid (e.g. *Myzus persicae* on sweet pepper) and whitefly (e.g. *Bemisia tabaci* on tomato) pests.

Optimal compositions, formulations and excipients may be defined as described herein for use in combination with plant activators and synergists to provide appropriate temporal exposure to maximize temporal synergistic effects.

DETAILED DISCLOSURE OF THE PREFERRED EMBODIMENTS OF THE INVENTION

Figure 1:
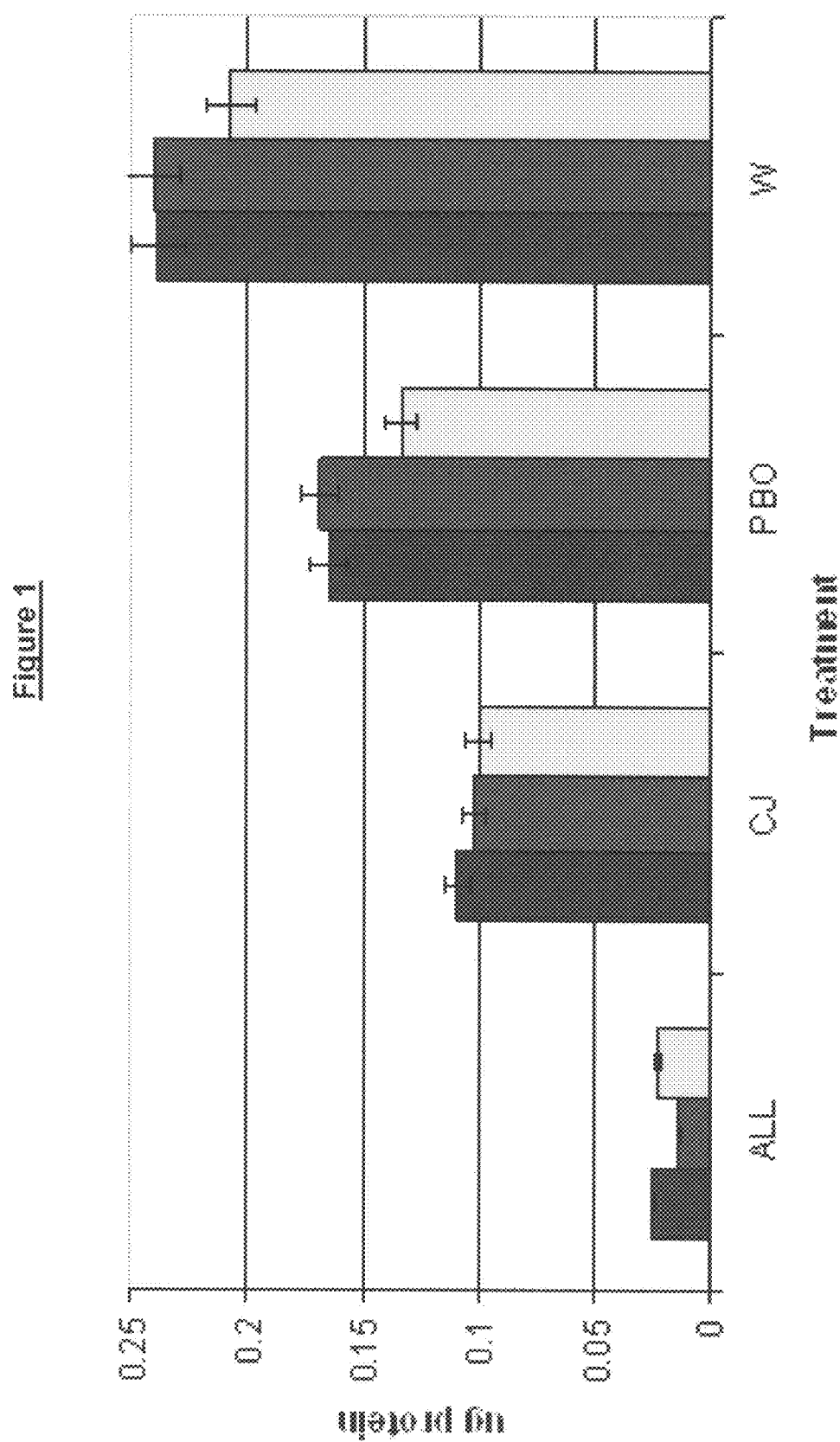
FIG. 1: The total amount of *B. tabaci* pupae protein (µg) collected from plants after ~16 days in the simulators trials, ten tomato plants per treatment with ten adult whiteflies per plant, results for weeks 1 to 3 are in dark, medium and light, respectively. All the treatments are significantly different to the control of deionised water (p<0.001) (see table 8 for statistical analysis data for all experiments).

Aspects of the invention provide methods and compositions for conferring protection on plants in a manner that can reduce, substantially reduce or eliminate the need for pesticides. This is particularly significant in light of the many reported instances of plant pests having developed resistance to known pesticides. The methods described herein, when used in combination with known pesticides, even those to which resistance in pests has developed, may result in synergistic potentiation of the impact of the pesticide.

An aspect of the invention provides a method of controlling plant pests which comprises; contacting a plant with one or more plant defence/insecticide synergists and one or more plant activators.

Treatment with the one or more plant defence/insecticide synergists and plant activators may reduce the susceptibility of the plant to pest damage; the amount of damage caused to a plant by a pest; the amount, frequency or duration of infestation of a plant by a plant pest; or the risk of infestation of the plant by the pest.

In some embodiments, the plant may be further contacted with a pesticide, and/or penetration promoting agent. In other embodiments, the plant may not be contacted with a pesticide, penetration promoting agent or additional active agents.

Preferably, the plant is not contacted with essential plant oils.

In some embodiments, the plant may be contacted with a formulation consisting essentially of one or more synergists, and one or more activators, and optionally, a pesticide, and/or a penetration promoting agent or facilitator.

In some embodiments, a suitable formulation may comprise additional components which have no material effect on the essential characteristics of the composition. For example, the formulation may comprise carriers, excipients and other inert compounds. A suitable formulation may be devoid of additional active components or may contain insufficient levels of additional active components to elicit any effect. Preferably, the formulation does not include essential plant oils.

A plant defence/insecticide synergist is a compound which inhibits, suppresses, or otherwise diminishes the ability of a plant pest to overcome, tolerate, deactivate or circumvent plant defence responses or pesticides. A suitable plant defence/insecticide synergist is non-toxic to the plant or the plant pest (i.e. the plant defence/insecticide synergist, on its own, may lack herbicidal or pesticidal activity).

Plant pests may, for example, circumvent plant defence responses and/or may circumvent pesticides through the over-production of esterases or oxidases or by mutation of pesticide targets in the pest.

Suitable plant defence/insecticide synergists for use in the present methods may include compounds which are esterase inhibitors; oxidase inhibitors; or both oxidase and esterase inhibitors.

In vitro biochemical tests for oxidase and esterase inhibitors are well known in the art and may readily be used to identify suitable plant defence/insecticide synergists.

Suitable plant defence/insecticide synergists may include compounds selected from the group consisting of an methylenedioxyphenyl (MDP) compound such as piperonyl butoxide (PBO) or an analog thereof, sesamex, sesamolin, sesamin, sulfoxide, tropital, propyl isome, MGK 264, propynyl phosphonate, N-isobutylundecylenamide, octachlorodipropyl ether and esters of gallic acid, including, for example, propyl gallate, or octyl gallate.

In some preferred embodiments, the one or more plant defence/insecticide synergists may be selected from the group consisting of an MDP compound, such as PBO or an analogue of PBO, and propyl gallate.

PBO (piperonyl butoxide: 2-(2-butoxyethoxy)ethyl 6-propylpiperonyl ether; CAS No: 51-03-6) is available from commercial sources (e.g. Endura SpA IT).

In some embodiments, an emulsified formulation of PBO may be used. Emulsified formulations may include micro-emulsified formulations. Emulsified formulations of PBO may be produced using conventional techniques. Typically, PBO is initially dissolved in an organic solvent, such as acetone, and then diluted into an aqueous solution containing a surfactant, for example a nonyl phenol ethylene oxide condensate such as Agral™. Alternatively, PBO may be supplied as an emulsifiable concentrate (for example, Enervate™, Nufarm Ltd, AU) which is mixed in aqueous diluent to form the emulsified PBO formulation.

Propyl gallate (Propyl 3,4,5-trihydroxybenzoate; CAS 121-79-9) or octyl gallate (3,4,5-Trihydroxybenzoic acid octyl ester; CAS 1034-01-1) may be preferred in some embodiments because they possess an established safety record from use in food products.

A plant activator is a compound which induces the plant to launch its own pest-defence mechanisms, for example by inducing the plant to produce or over-produce xenobiotics; directly repelling the plant pest; or by attracting to the plant organisms which target the plant pests (e.g. insect parasitoids). Suitable activators of plant pest defences are non-toxic to the plant and have no direct toxic effect on the plant pest (i.e. the plant activator, on its own, may lack herbicidal or pesticidal activity).

Suitable plant activators may be selected from the group consisting of cis-jasmone (CA 488-10-8) and analogues thereof, methyl jasmonate (Methyl (1R,2R)-3-Oxo-2-(2Z)-2-pentenyl-cyclopentaneacetate; CAS: 39924-52-2), methyl salicylate, salicylic acid and analogues thereof, and beta aminobutyric acid (BABA: CAS 2835-82-7).

Routine tests for plant activators are well known in the art and may readily be used to identify suitable compounds. For example, a plant may be contacted with the compound and the volatiles produced by the plant measured, for example by gas chromatography electroatomic graph, or the production of secondary metabolites may be measured, for example by HPLC.

In some preferred embodiments, the activator is cis-jasmone or an analogue thereof cis-jasmone is known to activate plants to produce xenobiotics which repel plant pests and to attract insect parasitoids. For example, a method of control of plant pests may comprise contacting a plant with PBO and cis-jasmone. The plant may be contacted simultaneously or sequentially with PBO and cis-jasmone, for example PBO may be applied before cis-jasmone.

In other preferred embodiments, the activator is BABA or an effective analogue thereof.

The one or more plant synergists and plant activators may be applied at an optimized regimen or temporal relationship to each other.

A regimen or temporal relationship may be optimized using routine experimentation.

For example, the one or more plant synergists may be applied to the plant at one or more of; before treatment with the one or more plant activators; after treatment with the one or more plant activators; and at the same time as treatment with the one or more plant activators.

The one or more plant synergists and the one or more plant activators may be applied at optimized dosages. Effective amounts (either as a single or multiple doses) of the one or more plant activators and plant synergists may be employed. For example, a plant activator such as cis-jasmone may be applied at a rate of 50.0 g cis-J/200 L/hectare, or 0.025 g/100 mL/plant. The appropriate dosage ranges may be selected and optimised using routine techniques by trial and error and bioassay, consistent with the teaching provided herein and the specifics of the examples provided below, without, at the same time, those specifics being taken as limiting.

Optionally, the one or more plant activators are administered in combination with a compound which promotes or facilitates the penetration of the activator into the plant.

Penetration promoting agents may be identified using routine techniques. For example, a non-toxic surfactant or wetting agent may be contacted with a plant in combination with a plant activator and the penetration of the activator into the plant measured in the presence of the agent relative to its absence. An increase in penetration in the presence of the surfactant or wetting agent is indicative that it is a penetration promoting agent.

Suitable penetration promoting agents include nonylphenol ethoxylate (Ethylan BV™ (EBV); Akcros Chemicals UK).

The methods described herein may be effective at controlling plant pests in the absence of a pesticide i.e. without applying to the plant any compounds which have a direct toxic effect on the pest.

In other embodiments, the effect of a pesticide on plant pests may be potentiated or increased using the present methods. This increase in pesticidal activity may be particularly useful for controlling plant pests which display resistance to the pesticide. The one or more plant synergists and activators may be administered, for example, in combination with a pesticide, for example an insecticide. Any pesticide which is registered for pesticide control on crops may be used for this purpose.

In some embodiments, the pest may display resistance to the pesticide in the absence of other agents (e.g. synergists and activators).

The plant pests which may be controlled using the methods described herein include insects, such as aphids, for example the green peach aphid (*Myzus persicae*), potato aphid (*Macrosiphum euphorbiae*), cotton bollworms (*Helicoverpa armigera*), and whitefly, for example the tobacco whitefly (*Bemisia tabaci*). For example, methods described herein may be useful to treat *Myzus persicae* on sweet pepper plants or *Bemisia tabaci* on tomato plants. Other plant pests include sucking pests, such as two spotted spider mite, potato leafhopper, lygus bug or western flower thrip; coeleopteran pests, such as the Colorado potato beetle, western corn rootworm, and southern corn rootworm; and lepidopteran pests, in particular caterpillars and larva, including larval wood moths (*Cossidae* spp), larval case moths (*Psychidae* spp) and looper caterpillars (*Millionia* spp).

A plant suitable for treating as described herein is preferably a higher plant, for example an agricultural plant selected from the group consisting of *Lithospermum erythrorhizon*, *Taxus* spp, tobacco, cucurbits, carrot, vegetable brassica, melons, capsicums, grape vines, lettuce, strawberry, oilseed brassica, sugar beet, wheat, barley, maize, rice, soyabeans, peas, sorghum, sunflower, tomato, potato, pepper, chrysanthemum, carnation, linseed, hemp, rye, cotton, black mustard, pepper and related brassicacea and colanacea.

Other plants suitable for treatment as described herein may include plants which display an elevated xenobiotic response through production of secondary metabolites, including glucosinolates.

The one or more plant synergists and plant activators may be applied to the plant by any convenient method, including spraying, atomizing, watering, introduction into the irrigation water, or any other suitable means for broadcasting or spreading the agents.

A population of plants may be treated as described herein. Another aspect of the invention provides a method of controlling plant pests in a plant population which comprises; contacting a population of plants with one or more plant synergists and one or more plant activators.

Treatment with the one or more plant synergists and plant activators may reduce the susceptibility of the plant population to pest damage; the amount of damage caused to a plant population by a pest; the amount, frequency or duration of infestation of a plant population by a plant pest; or the risk of infestation of the plant population by the pest.

Another aspect of the invention provides a composition which consists essentially of one or more plant synergists and one or more plant activators, but optionally also including a pesticide, a penetration promoting agent, or both.

A suitable composition may be devoid of additional active components or may contain minimal levels of such components which are insufficient for activity.

A suitable composition may comprise additional components which have no material effect on the essential characteristics of the composition. For example, the composition may comprise inert compounds such as carriers and excipients.

Preferably, the composition does not include essential plant oils.

Plant synergists, activators, pesticides and penetration promoting agents are described in more detail above. In some preferred embodiments, the composition may comprise PBO and cis-jasmone, and, optionally, nonylphenol ethoxylate (Ethylan BV; EBV).

The composition may provide for temporal control over the release of the one or more plant synergists, control over the release of the one or more plant activators, or control over release of both the one or more plant synergists and the one or more plant activators.

For example, the one or more synergists, the one or more activators or both may be encapsulated. Encapsulation may delay the release of either or both of the one or more synergists and the one or more plant activators, which may be released either simultaneously or separately.

For example, release of the one or more synergists from the composition may begin from up to 12 hours before the release of the one or more plant activators to up to 12 hours after release of the one or more plant activators. Release of the one or more synergists may end from up to 12 hours before the release of the one or more plant activators to up to 12 hours after release of the one or more plant activators.

The one or more plant activators and plant synergists may be released over a short time frame of minutes up to a period of release over several days.

The one or more synergists, the one or more activators or both may be encapsulated with any suitable encapsulant.

Suitable encapsulants are well known in the art and include cyclodextrins, yeast, gum acacia, polyurea, polyamide, capsule suspensions, such as the Zeon™ encapsulant used for Karate® (lambda-cyhalothrin; Syngenta), and combinations thereof. Other suitable encapsulants are described in WO06111553, WO06111570, EP17157392, WO06100308 and EP1742728.

The composition may be provided in any convenient form, for example an aqueous solution, a solid such as powder or granules or an aqueous dispersion. In some embodiments, the composition may be prepared in the form of a solid such as powder or granules, or an aqueous dispersion of high concentration which is diluted, for example with water, at the time of use so as to sprinkle or spray the diluted composition on the plants.

The composition may be prepared by a method known per se in the art, for example, by mixing and stirring the individual components.

The composition may further comprise carriers, solvents, pH adjustors, inorganic salts, thickeners, coloring matter, perfume bases, plant nutrients, spray drift retardants, stickers, spreaders, fertilizers, or viscosity modifiers as appropriate for the specific application.

The optimization of temporal synergy between the plant synergist and plant activator as described herein allows maximal effects to be achieved at minimal dosages. In addition, used in combination with pesticides, the plant protective effects of all of these compounds may be optimized.

Beneficial effects may also be achieved in animals which consume plants treated as described herein. For example, residual materials may be ingested by animals, thereby reducing pest infestation of the animals and/or xenobiotics produced by plants after treatment as described herein may be ingested by animals and elicit beneficial effects in the animals.

Those skilled in the art will appreciate that other applications and benefits according to the invention may be achieved by utilizing the herein disclosed methods and compositions.

The invention is generally described herein, including how to make and use the compounds, compositions and combinations thereof, and the best mode for release of compounds to achieve optimal results. Various further aspects and embodiments of the present invention will be apparent to those skilled in the art in view of the present disclosure. The following examples are provided to extend the written description and enablement of this invention. However, those skilled in the art will appreciate that the invention is not restricted to the specifics of the examples provided. Rather, for the scope of the invention encompassed by this disclosure, reference should be had to the claims and the equivalents thereof appended to this disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above and tables described below.

EXPERIMENTS

1. Summary

The plant pests analyzed in the examples provided herein include *Myzus persicae* on pepper, which we demonstrate had a reduced amount of protein on the plant when treated with cis-jasmone, and this effect increased with the addition of PBO. This was true of small scale assays with three plants when 10, 5, or 1 adult aphid was added to each plant at the beginning of the experiment. PBO alone gave no significant reduction in total aphid protein; and Ethylan BV (EBV, an adjuvant to aid transport of cis-jasmone through physical barriers) alone gave no significant reduction either. The application of both PBO and cis-jasmone gave a highly significant decrease in aphid protein ($P<0.001$).

The effects on *B. tabaci* gave a similar result with there being very close to zero protein on the plant in the small scale bioassays. When this was scaled up to the glasshouse simulators, 25 pepper plants and 10 tomato plants per treatment, the effects were the same, with all treatments with cis-jasmone and cis-jasmone with PBO having significantly less insect protein on the plants ($P=0.002$ and $P<0.001$ for *M. persicae* and *B. tabaci* respectively).

Glasshouse simulators gave good results, indicating this concept could be scaled up to field plots. The addition of PBO potentiates the effect of cis-jasmone, i.e. there is a synergism of the cis-jasmone treatment, and so there is more than an additional effect on the reduction of insect protein when the two are mixed and the plants treated ($p<0.001$ for *B. tabaci* and $p=0.002$ in *M. persicae*). This is true with both *Myzus persicae* on pepper plants and *Bemisia tabaci* on tomato plants.

A reduced amount of *Bemisia tabaci* and *Myzus persicae* protein is also demonstrated in the examples on potato, cotton and *Brassica* plants treated with BABA, and this effect is synergistically increased with the addition of PBO.

2. Materials and Methods 2.1 Cis-Jasmone and PBO

Apterous and alate individuals of an insecticide-susceptible strain of *Myzus persicae*, US1L, were produced and maintained on sweet pepper, variety 'Bell Boy'. An insecticide-resistant strain of *Bemisia tabaci*, GUA MIX, was established on tomato plants, variety 'Carousel' (commercially grown) in the laboratory. Statistical analysis was done using Genstat 10.

In all bioassay experiments the control plants were sprayed with deionised water. Initially seven treatments were used (Table 1) to test all chemical variables. All treatments were applied hydraulically with a spray simulator after which the plants were separated according to treatment (with cis-jasmone controls being separated) and left for 2 hours prior to insect application.

Analysis of protein in each treatment was conducted using Bradford Reagent: the data were analysed using the computer programme 'GraFit' (Erithacus software, Berkeley). To calculate the calibration curve a single logarithmic curve was used with regression analysis taking the values of the treatment wells (averages of the three readings taken: technical replicates).

The amounts of cis-jasmone and Ethylan BV (EBV) are shown in Table 1a below. These were tested and cis-jasmone found to be effective in reducing total insect protein on the plants. EBV had no effect alone. Experiments using an optimal concentration of PBO for esterase inhibition established 1000 ppm as appropriate.

Laboratory and simulator tests were undertaken to compare effects of combined and single treatments of PBO and cis-jasmone on control of aphid (*M. persicae*) on sweet pepper and whitefly (*B. tabaci*) on tomato. All tests included untreated and blank (water plus emulsifier/wetting agent) controls, and both single and combined applications of PBO and cis-jasmone.

Investigating developmental/fecundity effects on *B. tabaci* of cis-jasmone applied to tomatoes, it was estimated that volatile effects of cis-jasmone would begin ~48 hours after treatment (for treatments see Table 1a)

A new method for the investigation of the development of whitefly to the pupal stage on tomatoes and cotton was used. This involved releasing 10 adult females on to each tomato plant which generated enough pupae for the test following removal by a scalpel blade. These were checked for protein after ~16 days using Bradford reagent.

Adults were added to the plant 2 h after treatment, and removed after 24 h. The eggs laid were then left for 16-18 days until they reached the pupal stage. The total pupal protein on the plant was tested using the Bradford reagent.

It has been shown that adults take up a small amount of plant protein particularly upon emergence. Therefore, to minimise this effect, the pupal stage was used.

To investigate developmental/fecundity effects of cis-jasmone+/−PBO (see Table 1) on *Myzus persicae* when applied to sweet peppers, adults were added to the plants and then using Bradford reagent, the amount of aphid protein present on the plants 7 days after treatment was measured. Esterase levels were also tested after the same interval to check for the possible induction of metabolic enzymes when using cis-jasmone. Aphids were brushed from all plants and each leaf checked individually to ensure none remained. The aphid mass for each treatment was weighed before total protein was assessed (total from all three plants in the treatment).

With *Myzus persicae* 10 adult aphids were initially added to each of the three plants. This was found to generate too much protein, but the effect was good—showing a large reduction in protein content when cis-jasmone was applied (for treatments see Table 1). The number was then reduced to one adult per plant and then five adults per plant and these gave promising results. Treatments of PBO technical grade and acetone were discontinued, as emulsified PBO was closer to the formulation likely to be used in the field. The EBV was also discontinued as this did not give a significant difference to the water control with five aphids/plant.

The effects of treatments in both bioassays and simulator trials were comparable in the two insect species tested. In all tests cis-jasmone treatments reduced the amount of insect protein significantly to that found in the deionised water treatment ($p<0.001$ for *B. tabaci* and $p=0.002$ in *M. persicae*) (see table 8 for statistical analysis data for all experiments).

In table 2 and 3 below the average insect protein content is given for each treatment and the week in which the experiment was conducted.

In the tables, the abbreviations are as follows:
ALL=cis-jasmone+emulsified PBO (PBO E),
CJ+PBO+Acetone+EBV=cis-jasmone+PBO Technical (97%)+Acetone (analytical grade)+EBV
CJ=cis-jasmone+EBV,
PBO=emulsified PBO (PBO E) only
PBO T+Acetone=PBO Technical (97%)+Acetone (analytical grade) and
W=deionised water.

Note that PBO technical grade was dissolved in acetone due to insolubility of PBO T in water. Cis-jasmone is volatile and is also not water soluble. It was mixed with EBV and then dissolved in water. Emulsified PBO (PBO E) already contains emulsifier, therefore cis-jasmone+PBO E does not require addition of EBV.

2.2 BABA and PBO

Using example crops of brassica [*Brassica nigra*] and potato [*Solanum tuberosum*]; BABA was added as a drench to the roots to 'prime' the plants in a series of concentrations (1-10 mM). The plants were artificially infested with a set number of first instar aphids (characterised as insecticide-resistant or -susceptible) and left for 1 week. At the end of this period, all aphids were removed and weighed to determine the growth of the population. This identified the optimal concentration of BABA to use to produce maximum secondary metabolites within the plant. All concentrations were lower than that which could cause direct damage to the crop. 3 mM BABA was identified as optimal for the conditions employed.

Insecticide-resistant *Myzus persicae* possess an enhanced non-specific esterase, E4, that can hydrolyse or/and sequester insecticides and plant xenobiotics. For optimal effects of the secondary metabolites from the crops to affect aphid mortality, this enzyme is preferably fully inhibited prior to exposure. This inhibition was achieved using the synergist piperonyl butoxide, PBO, a chemical that was originally thought to be a specific inhibitor of microsomal oxidases, but has now been shown to also inhibit esterases. The esterase activity of individuals from a clone of resistant *Myzus persicae* was measured at zero time, then at hourly intervals following in vivo topical application of 1 ul of 0.1% PBO. When individual whiteflies (*Bemisia tabaci*) were treated in this fashion, the optimal time delay was found to be 10 hours. When individual cotton bollworms (*Helicoverpa armigera*) were treated similarly, the time delay was found to be 5 hours. The assay would also be continued to determine the time taken for the esterase levels to return to normal.

In all bioassay experiments the control plants were sprayed with deionised water. Initially seven treatments were used (Table 1b) to test all chemical variables. All treatments were applied hydraulically with a spray simulator after which the plants were separated according to treatment and left for 2 hours prior to insect application.

Analysis of protein in each treatment was conducted using Bradford Reagent: the data were analysed using the computer programme 'GraFit' (Erithacus software, Berkeley). To calculate the calibration curve a single logarithmic curve was used with regression analysis taking the values of the treatment wells (averages of the three readings taken: technical replicates).

Laboratory tests were undertaken to compare effects of combined and single treatments of PBO and BABA on control of aphid (*M. persicae*) on potato, pepper, and black mustard and whitefly (*B. tabaci*) on cotton and tomato. All tests included untreated and blank (water) controls, and both single and combined applications of PBO and BABA. The amounts of BABA and PBO are shown in Table 1b below. These were tested and BABA found to be effective in reducing total insect protein on the plants.

The development of whitefly to the pupal stage on tomatoes and cotton was investigated by releasing 10 adult females on to each tomato/cotton plant which generated enough pupae for the test following removal by a scalpel blade. These were checked for protein after ~16 days using Bradford reagent.

Adults were added to the plant 2 days after treatment, and removed after 24 h. The eggs laid were then left for 16-18 days until they reached the pupal stage. The total pupal protein on the plant was tested using the Bradford reagent.

The pupal stage was tested because adults are known to take up a small amount of plant protein, particularly upon emergence. Use of the pupal stage minimised this effect.

To investigate developmental/fecundity effects of BABA+/−PBO E (see Table 1) on *Myzus persicae* when applied to plants, adults were added to the plants and then using Bradford reagent, the amount of aphid protein present on the plants 7 days after treatment was measured. Esterase levels were also tested after the same interval to check for the possible induction of metabolic enzymes when using BABA. Aphids were brushed from all plants and each leaf checked individually to ensure none remained. The aphid mass for each treatment was weighed before total protein was assessed (total from all five plants in the treatment).

3. Results 3.1. Effects on *B. tabaci* Pupae Protein (μg) Collected from Tomato Plants Treated with Cis-Jasmone and PBO As described above 10 adult females were released on to each tomato plant, ten/treatment and after ~16 days pupae were removed using a scalpel blade. These were checked for total protein using Bradford reagent. Plants were put into glasshouse simulators (one/treatment) and kept at 28° C., 12 L: 16 D and 80% R.H.

In FIG. 1, it can be seen that all the treatments are significantly different to the control of deionised water (p<0.001) (see table 8 for statistical analysis data for all experiments Table 2 shows the total amount of *B. tabaci* pupae protein (μg) collected from plants after ~16 days in the simulators trials, ten tomato plants per treatment with ten adult whiteflies per plant, results for weeks 1 to 3.

The addition of PBO potentiates the effect of cis-jasmone, there is a synergism of the cis-jasmone, and so more than an additional effect on the reduction of insect protein when the two are mixed and the plants treated.

3.2. *M. persicae* Protein (μg) Collected from Pepper Plants after 7 Days Treatment with Cis-Jasmone and PBO

*Myzus persicae* were applied to sweet peppers at the rate of three adults per plant. Aphids were brushed from all plants and each leaf checked individually to ensure none remained. The aphid mass for each treatment was assessed for total protein (total from all 25 plants in the treatment) using Bradford reagent. The amount of aphid protein present on the plants 7 days after treatment was measured. Plants were put into glasshouse simulators (one/treatment) and kept at 28° C., 12 L: 16 D and 80% R.H.

Table 3 shows the total amount of *M. persicae* protein (μg) collected from plants after 7 days in the simulators trials, 25 pepper plants per treatment with three adult apterous aphids per plant, results for weeks 1 to 3. The difference in total protein when cis-jasmone+/−PBO is applied to the plants is significantly different to that of both controls PBO and deionised water (p=0.002) (see table 8 for statistical analysis data for all experiments). However in this case the addition of PBO to cis jasmone does not significantly increase efficacy.

Figure 2:
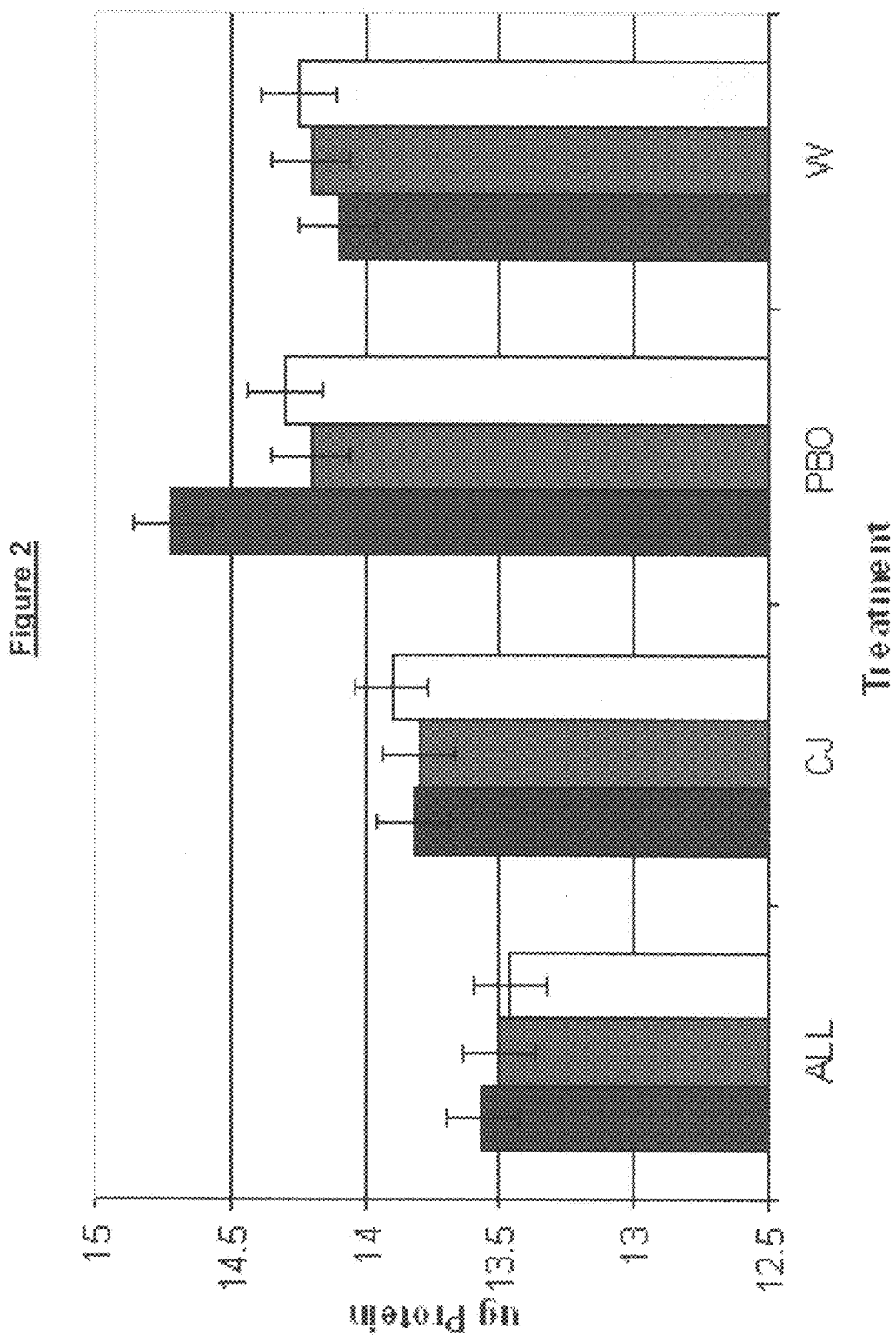
FIG. 2: The total amount of *M. persicae* protein (µg) collected from plants after 7 days in the simulators trials, 25 pepper plants per treatment with three adult apterous aphids per plant; results for weeks 1 to 3 are in dark, medium and light respectively.

In FIG. 2, in week 1 of trials, the amount of protein with the treatment of PBO is significantly higher than either week 2 or 3. This effect is not reflected in the other treatments in week one. The result is particularly surprising since Devine et al (1998) has shown that PBO had an effect similar to an insect growth regulator on *B. tabaci*. It is not clear if this effect is transferable to aphids as well, but an increase in protein is an unlikely effect. Therefore it is likely that this is an anomaly. In FIG. 2, it is clearer to see that the two cis-jasmone treatments significantly reduce the amount of total insect protein.

3.3. *M. persicae* Protein (μg) Collected from Pepper Plants after 7 Days Treatment with Cis-Jasmone and PBO To investigate developmental/fecundity effects of cis-jasmone+/−PBO E on *Myzus persicae* when applied to sweet peppers, one adult was added to the plants. Aphids were brushed from all plants and each leaf checked individually to ensure none remained. The aphid mass for each treatment was assessed for total protein (total from all four plants in the treatment) using Bradford reagent. The amount of aphid protein present on the plants 7 days after treatment was measured.

With *Myzus persicae*, 10 adult aphids were initially added to each of the three plants. This was found to generate too much protein, but the effect was good—showing a large reduction in protein content when cis-jasmone was applied (for treatments see Table 1).

The number was then reduced to one adult per plant and then five adults per plant and these gave promising results. Treatments of PBO technical grade and acetone were discontinued, as emulsified PBO was closer to the formulation likely to be used in the field. The use of EBV was also discontinued as this did not give a significant difference to the water control with five aphids/plant.

Table 4 shows the total amount of *M. persicae* protein (μg) collected from plants after 7 days in the bioassay with four pepper plants and one adult apterous aphid added to each plant, results for weeks 1 to 3. The results follow those found in the simulator trials with cis-jasmone treated plants having significantly reduced total insect protein (p<0.001) (see table 8 for statistical analysis data for all experiments).

In the bioassays, there were a larger number of treatments, as different formulations and effects of emulsifiers were examined, before being ruled out.

Also in this set of bioassays, over three weeks—as with the simulator trials, there does seem to be a difference in the weeks that treatments were carried out. All methods were conducted in the same manner in each week. The fact that this is on a much smaller scale than the simulators could explain it, as there are a much smaller number of plants per replicate, suggesting that the larger scale simulators are a much better test of the treatments.

Figure 3:
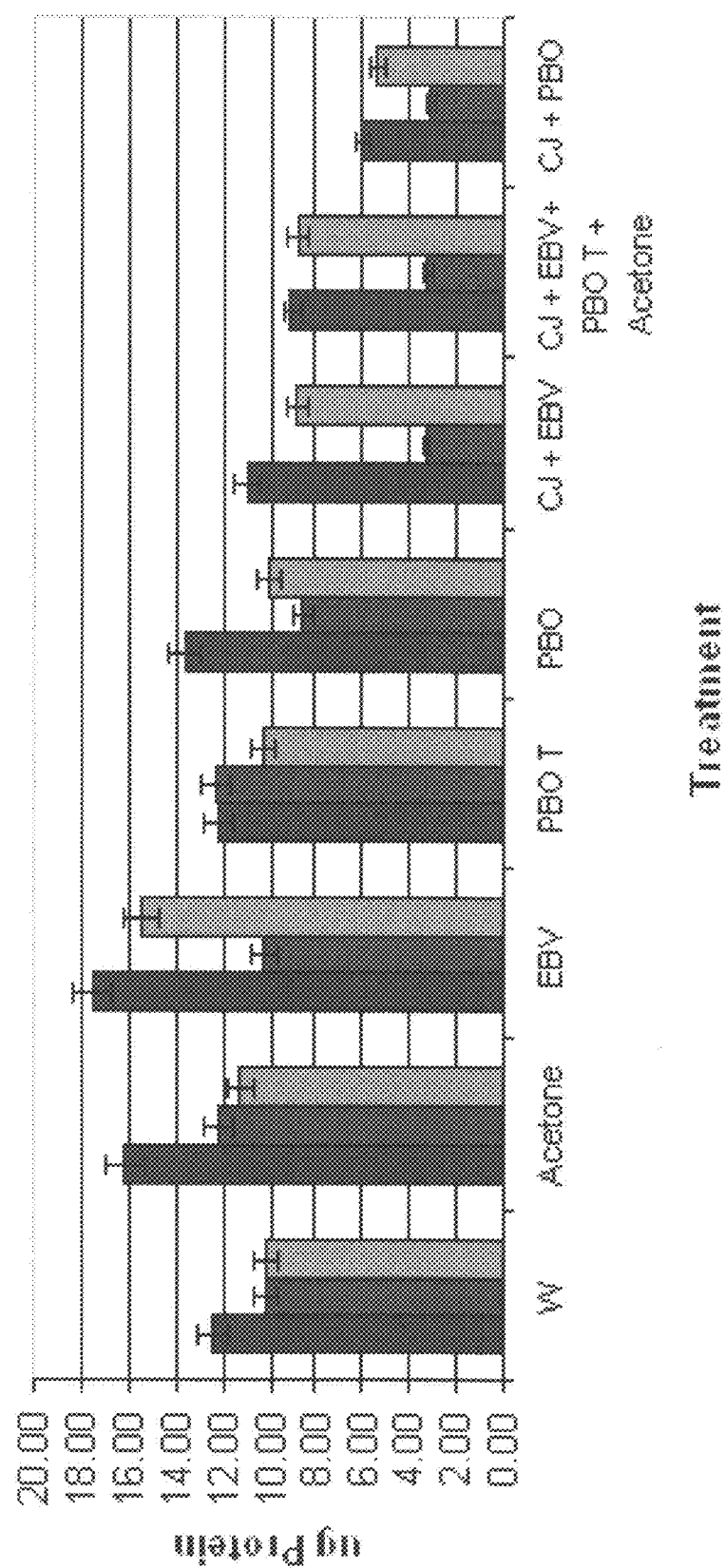
FIG. 3: The total amount of *M. persicae* protein (µg) collected from plants after 7 days in the bioassay with four pepper plants and one adult apterous aphid added to each plant; results for weeks 1 to 3 are in dark, medium and light respectively.

In FIG. 3, the difference between the week is quite clear, but the cis-jasmone treatments are still significantly different to the deionised water control (p<0.001) (see table 8 for statistical analysis data for all experiments).

Also the fact that only one adult aphid is added to each plant will increase the differentiation between weeks, because although the adult aphids are all similar in size and age there are some small differences and this will lead to difference in nymphs produced and size and therefore total protein in each week after treatments were applied. These differences indicate that one adult per plant is too few to add, this and the following bioassays (tables 4 and 5) indicated that 3-4 aphids per plant would be the best number to work with—hence three adults per plant was the number chosen for the simulator trials.

3.4. *M. persicae* Protein (μg) Collected from Pepper Plants after 7 Days Treatment with Cis-Jasmone and PBO

*Myzus persicae* was applied to sweet peppers at the rate of five adults were added per plant. Aphids were brushed from all plants and each leaf checked individually to ensure none remained. The aphid mass for each treatment was assessed for total protein (total from all four plants in the treatment) using Bradford reagent. The amount of aphid protein present on the plants 7 days after treatment was measured (for further information see Example 3).

Figure 4:
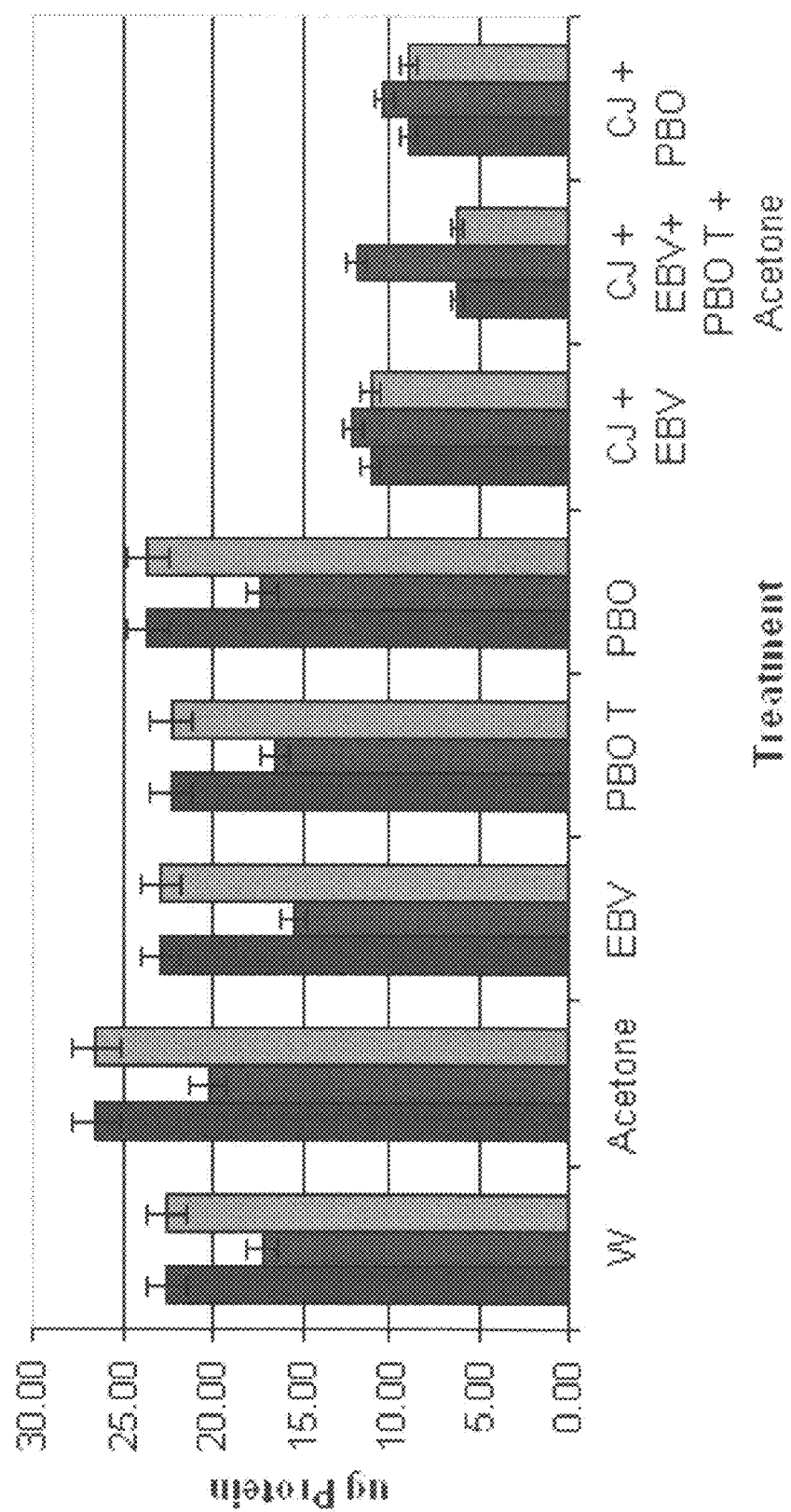
FIG. 4: The total amount of *M. persicae* protein (µg) collected from plants after 7 days in the bioassay with four pepper plants and five adult apterous aphid added to each plant, results for weeks 1 to 3 are in dark, medium and light respectively.

Table 5 shows the total amount of *M. persicae* protein (μg) collected from plants after 7 days in the bioassay with four pepper plants and five adult apterous aphids added to each plant, results for weeks 1 to 3. There is a significant difference (see FIG. 4) between all treatments containing cis-jasmone and all controls (includes PBO, PBO T and EBV along with W) (p<0.001) (see table 8 for statistical analysis data for all experiments).

There is some differentiation between weeks but it is somewhat less, the small number of plants could again be the reason for this. The addition of PBO potentiates the effect of cis-jasmone, not to the extent of the *B. tabaci* data, but there is more than an additional effect on the reduction of insect protein here.

3.5. *M. persicae* Protein (μg) Collected from Pepper Plants after 7 Days Treatment with Cis-Jasmone and PBO

*Myzus persicae* were applied to sweet peppers at the rate of ten adults per plant. Aphids were brushed from all plants and each leaf checked individually to ensure none remained. The aphid mass for each treatment was assessed for total protein (total from all four plants in the treatment) using Bradford reagent. The amount of aphid protein present on the plants 7 days after treatment was measured (for further information see Example 3).

Table 6 shows the total amount of *M. persicae* protein (μg) collected from plants after 7 days in the bioassay with four pepper plants and ten adult apterous aphids added to each plant, results for weeks 1 to 3. Again there is a significant reduction of protein with cis-jasmone treatments ($p<0.001$) when compared with the control of deionised water (see table 8 for all statistical analysis data).

Figure 5:
FIG. 5: The total amount of *M. persicae* protein (µg) collected from plants after 7 days in the bioassay with four pepper plants and ten adult apterous aphids added to each plant; results for weeks 1 to 3 are in dark, medium and light respectively.

FIG. 5 shows the total amount of *M. persicae* protein (μg) collected from plants after 7 days in the bioassay with four pepper plants and ten adult apterous aphids added to each plant, results for weeks 1 to 3 are in dark, medium and light respectively.

3.6. *B. tabaci* Pupae Protein (μg) Collected from Tomato Plants after ~16 Days Treatment with Cis-Jasmone and PBO The amount of insect protein per treatment when ten aphids were added to each plant was very large compared with adding five and one aphid at the beginning of the bioassay. When calculating the μg of insect protein from the calibration curve in the grafit programme, it was difficult to add enough bovine serum albumin to get high enough values to extrapolate the curve against the bioassay values. Therefore, a straight line rather than a curve was used. This gave less accurate data, and so indicated a lower number of aphids per plant was required for the simulator trials. The values were however still significantly different when comparing cis-jasmone treatments to all controls and also cis-jasmone+PBO was significant better at reducing the total protein than the other two cis-jasmone treatments ($p<0.001$).

Table 7 shows the total amount of *B. tabaci* pupae protein (μg) collected from plants after ~16 days in the bioassay with one tomato plant and ten adult whiteflies added to the plant, results for weeks 1 to 3. There is a clear and highly significant ($p<0.001$) synergistic effect of adding PBO to the cis-jasmone treatment.

Figure 6:
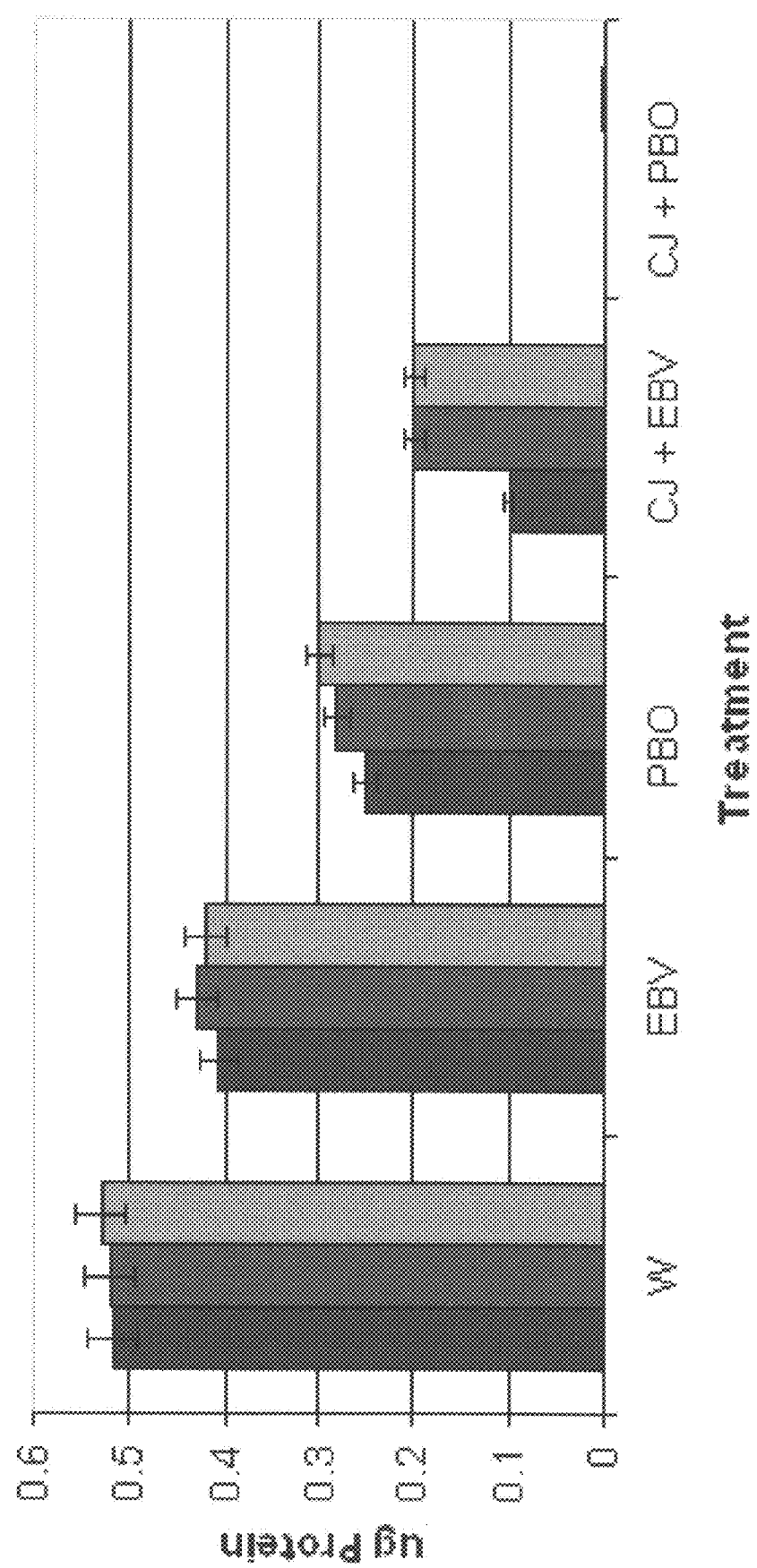
FIG. 6: The total amount of *B. tabaci* pupae protein (µg) collected from plants after ~16 days in the bioassay with one tomato plant and ten adult whiteflies added to the plant, results for weeks 1 to 3 are in dark, medium and light, respectively.

In FIG. 6 it can be seen that all the treatments are significantly different to the control of deionised water ($p<0.001$) (see table 8 for statistical analysis data for all experiments).

Also each treatment is significantly different ($p<0.001$) from each other, clearly see below with the reducing amounts of total protein down to ~0 μg for cis-jasmone+PBO.

3.7. Statistical Analysis

The addition of PBO potentiates the effect of cis-jasmone. There is more than an additional effect on the reduction of insect protein (i.e. a synergism) when the two are mixed and the plants treated.

Table 8 shows all the above results for the average total insect protein (μg) for all treatments along with the results of the statistical analysis from Genstat 10, using one way ANOVA in a randomized block design. SEM stands for standard errors of means, LSD stands for least significant differences of means (5% level) and DF is degrees of freedom.

Figure 7:
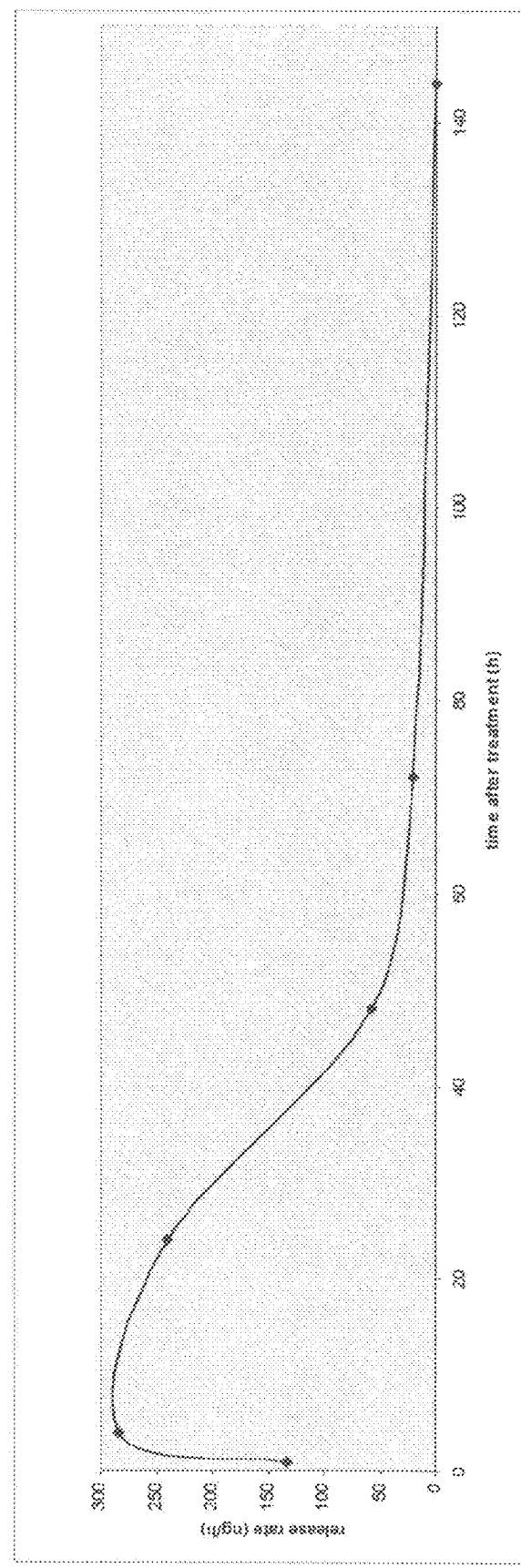
FIG. 7: Emission of cis-Jasmone from rape plant treated with cyclodextrin microencapsulated cis-Jasmone
Figure 8:
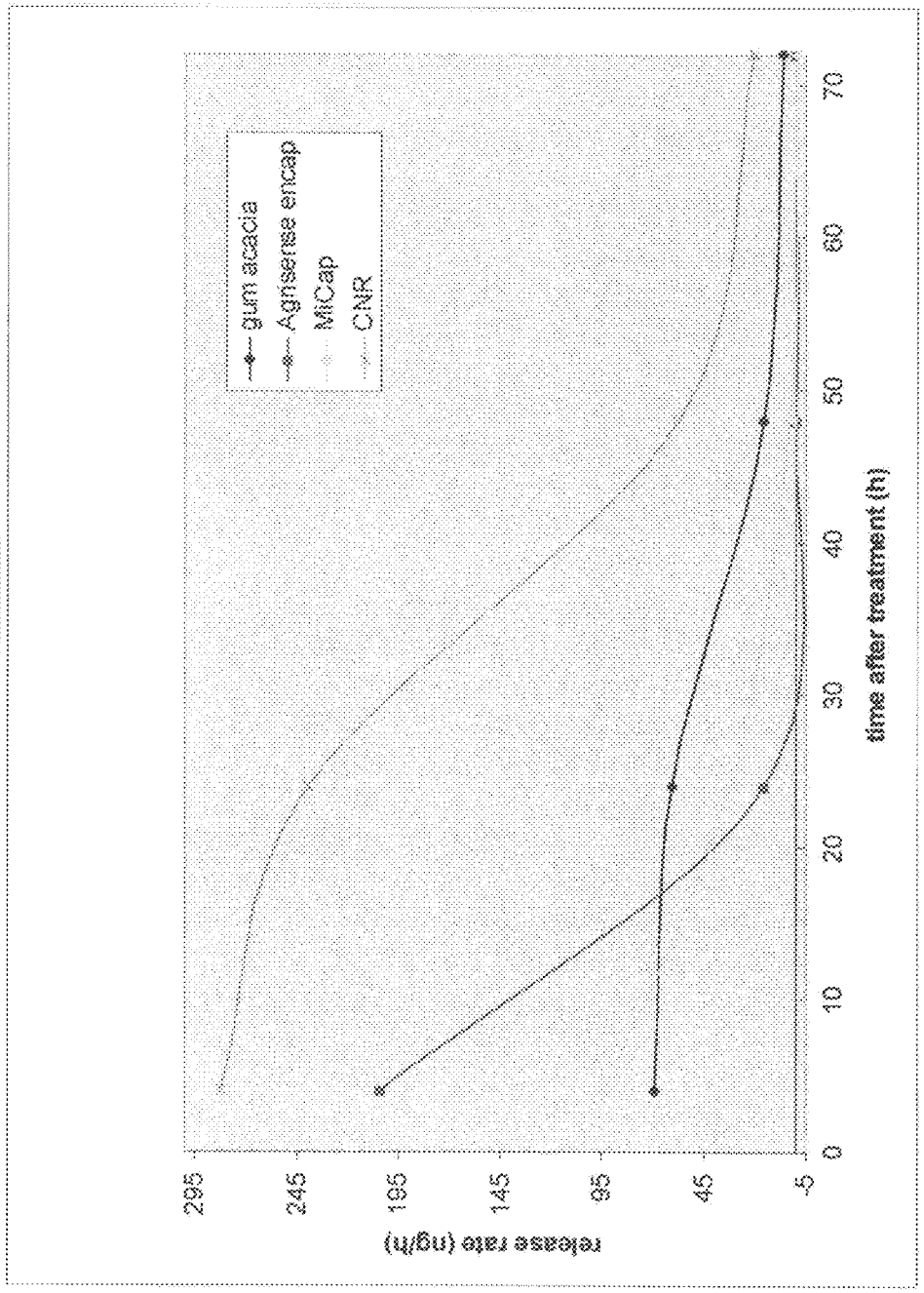
FIG. 8: Emission of cis-Jasmone from rape plant treated with different formulations

3.8. Sustained Release Formulations and Effects of Combined Synergists and Activators FIGS. 7 and 8 provide release rate data for microencapsulated cis-jasmone. It could not be detected after 6 days when encapsulated in cyclodextrin, but could be detected when formulated with gum acacia which gave good sustained release up to at least 72 h.

The slow release cis-jasmone formulations were sprayed onto a rape plant using a track sprayer. The sprayer applied treatments to plants in the same way a tractor boom would in the field.

Rape plants in the vegetative growth stage were chosen because they do not release many volatiles themselves but provide the advantage over inert substrates that we have used previously in that release from the formulation being tested is from an actual plant which is more realistic as the formulation is intended for crop protection end use.

All formulations were at 50.0 g active ingredient per hectare in 200 liters per hectare. For treatment of one plant, a 100 ml solution in distilled water was made for use in the track sprayer which contained 0.025 g of cis-jasmone. Microencapsulated formulations were supplied with information on the percentage cis-jasmone content. From this, the amount required to mix with the 100 ml water to provide 0.025 g of cis-jasmone was calculated. For example with the CNR material tested cis jasmone content was 7.5% which was prepared by weighing out 0.3333 g to go in 100 ml. The same applied to the Agrisense™, MiCap and gum acacia formulations. The CNR formulation was a cyclodextrin based microencapsulation. The Agrisense formulation (Suterra LLC, OR, USA) was 5.77% cis jasmone with 94.23 inert carrier. The MiCap formulation was yeast (Saccharomyces cerevisiae) based microencapsulation which was 34% cis-jasmone. For gum acacia, a 3% gum acacia solution was used. However, this formulation proved to be difficult to handle when applied under field conditions—the 3% formulation gummed up the tractor tank at low temperature. This formulation may be refined by reducing the amount of gum used, recognizing this may affect the release rate profile. Gum acacia was added to an aqueous solution before the cis-jasmone was added. 0.025 g cis-jasmone was then added to 100 ml of the aqueous gum acacia solution.

In summary, for each of the formulations tested: Cis jasmone was used at a rate of 50.0 g cis-J/200 L/hectare, or 0.025 g/100 mL/plant. CNR=7.5% cis-J in cyclodextrin—(see WO 06111570 and EP 17157392); MiCAP=34% cis-J in *S. cerevisiae*—(see WO 06100308 and EP1742728); Agrisense=5.77% cis-J; Gum Acacia=cis-J in 3% gum acacia (although the gum acacia concentration may be modified to optimize application properties).

The collection of volatiles from the plant is a measure of the release of cis-jasmone from the formulation. Plants with similar sized leaves were selected when possible so that the area from which the formulations were released was kept relatively constant. 50 g cis-jasmone in 200 l/ha was used as an application rate, with 0.025 g in 100 ml being used as an equivalent to this for a single plant. The gum acacia formulation is equivalent to 50 g cis jasmone in 3% gum acacia in 200 l/ha (equals 6 kg/ha gum acacia).

As the cis jasmone is the volatile component of the composition being administered, it is a good indicator of the operation of the present methods when one or both of the components (synergist and/or activator) are volatile. The non-volatile component is expected to be released from the formulations according to this invention in ways that those skilled in the art can modify and adapt without undue experimentation to achieved desirable relative release rates.

3.9. *B. tabaci* Pupae Protein (μg) Collected from Cotton Plants after ~16 Days of Treatment with PBO and/or Microencapsulated Cis-Jasmone Table 9 shows the total amount of *B. tabaci* pupae protein (μg) collected from plants after ~16 days, five cotton plants per treatment with 5 adult female whiteflies per plant, results for weeks 1 to 3.

Figure 9:
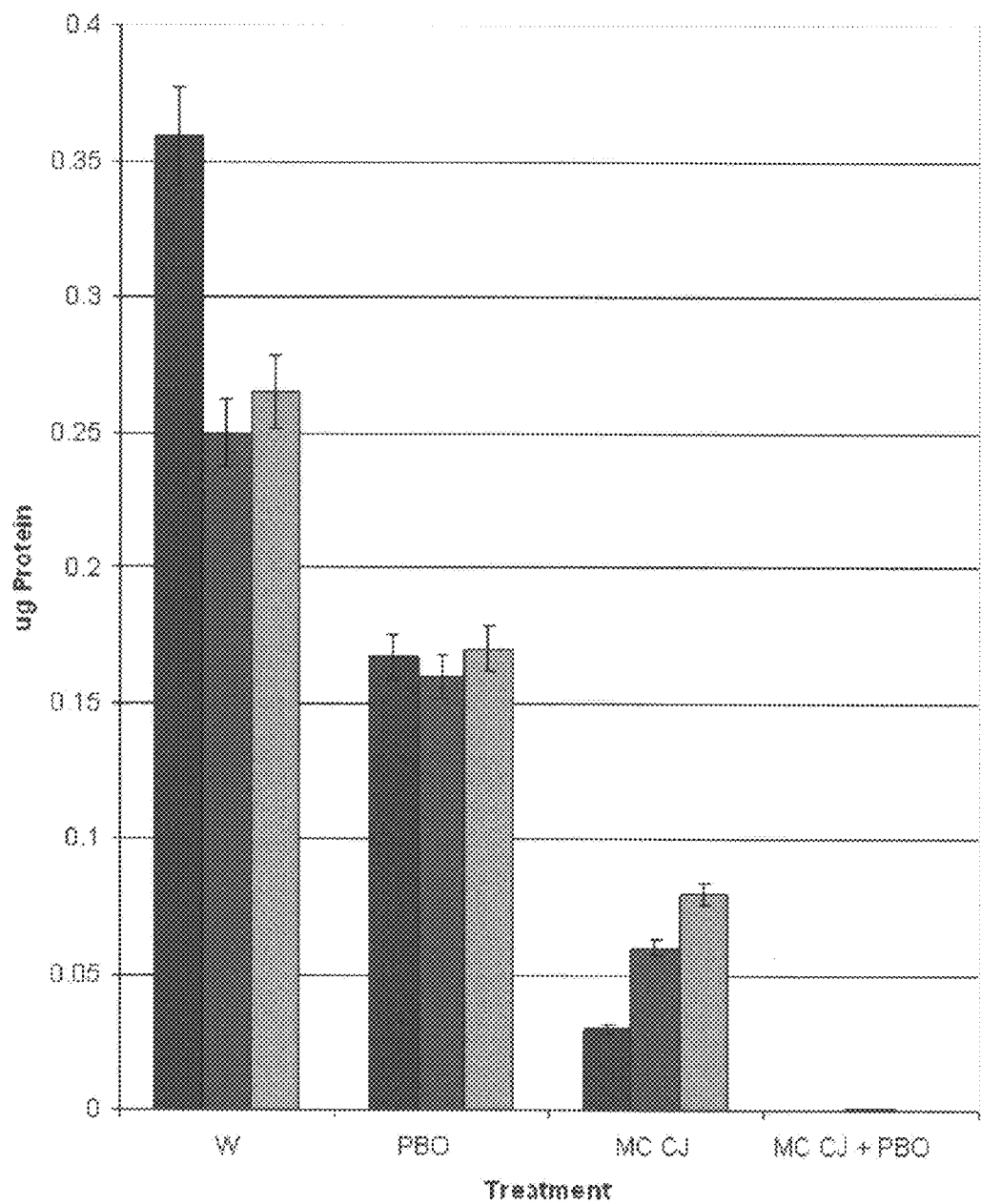
FIG. 9: Total amount of *B. tabaci* pupae protein (µg) collected from plants after ~16 days, five cotton plants per treatment with 5 adult whiteflies per plant, results for weeks 1 to 3.

Table 9 and FIG. 9 show that the addition of PBO potentiates the effect of this new microencapsulated cis-jasmone, there is a synergism of the cis-jasmone. The effect is as good on cotton as on tomatoes. Also this new microencapsulated formulation is as effective as the previous EBV formulation with cis-jasmone.

3.10. Effects of Propyl Gallate and Cis-Jasmone on *A. gossypii* Nymphs (μg) Collected from Plants Table 10 shows the total amount of *A. gossypii* protein (μg) collected from cotton plants after 7 days in the bioassay with five cotton plants and 3 adult apterous aphids added to each plant, results for weeks 1 to 3.

Figure 10:
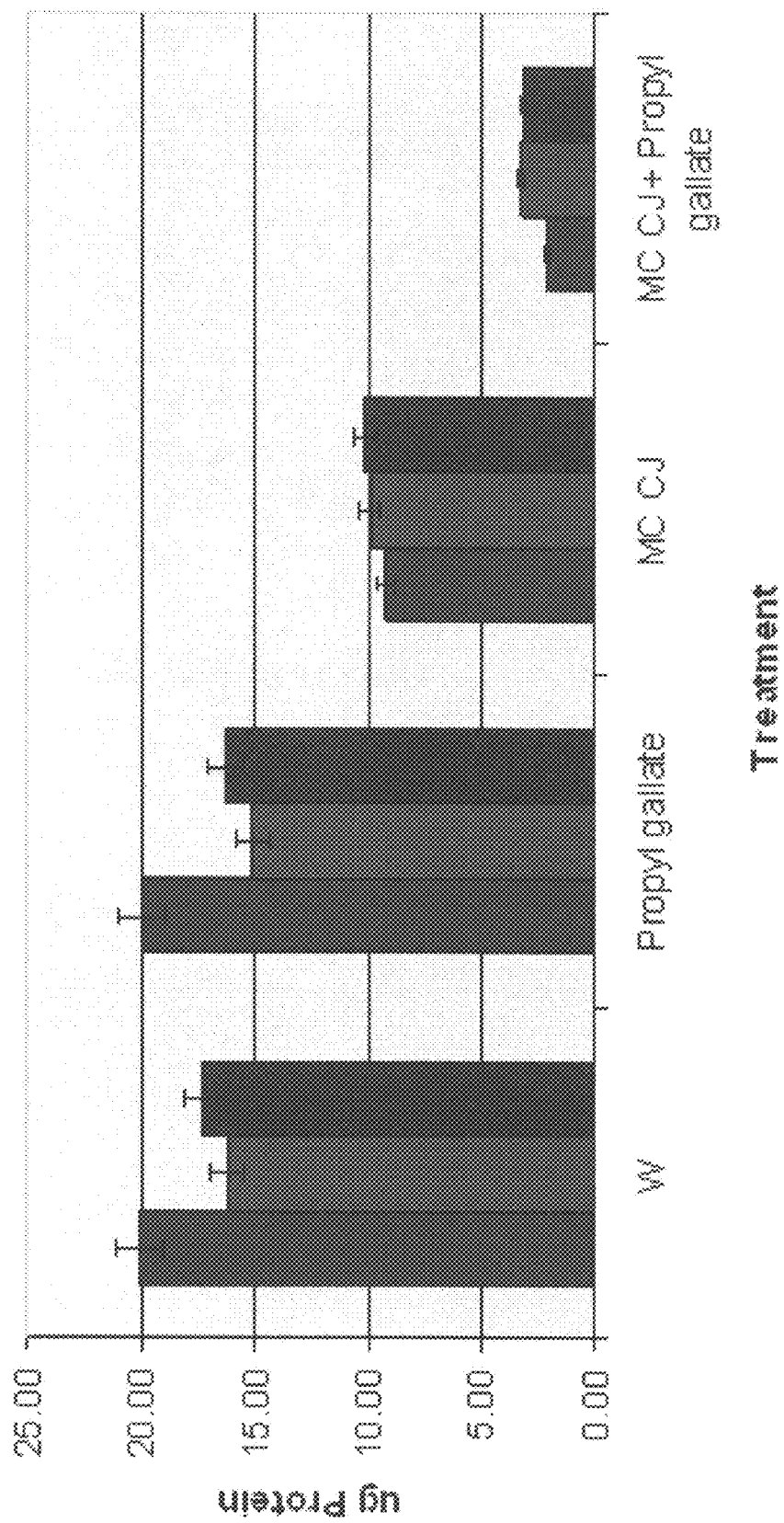
FIG. 10: Total amount of *Aphis gossypii* protein (µg) collected from cotton plants after 7 days in the bioassay with five cotton plants and 3 adult apterous aphid added to each plant, results for weeks 1 to 3; after addition of propyl gallate, CJ, and propyl Gallate+CJ.
Figure 11:
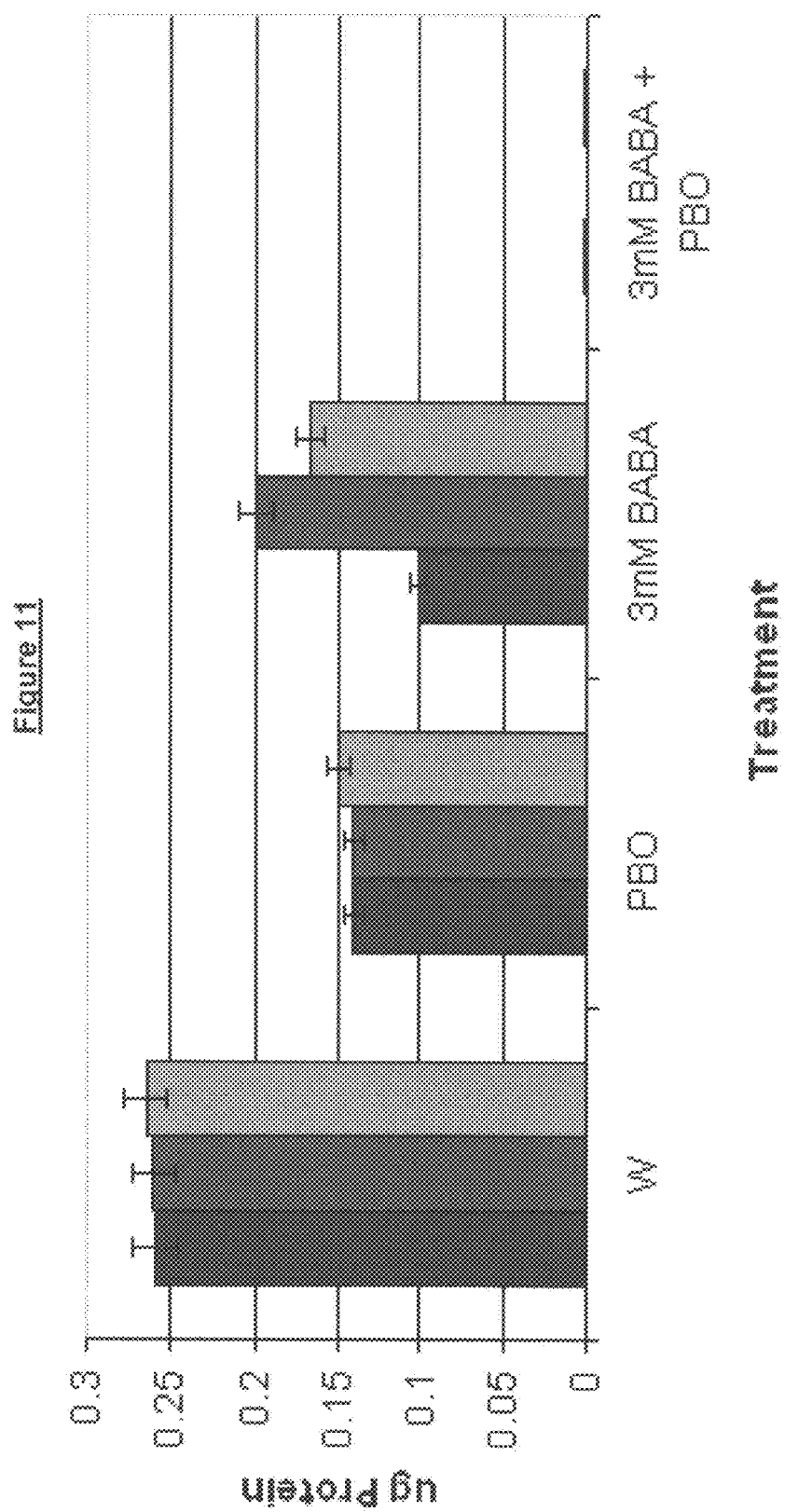
FIG. 11: Total amount of *B. tabaci* pupae protein (µg) collected from cotton plants after ~16 days in the bioassay with five cotton plants and 3 adult apterous aphid added to each plant, results for weeks 1 to 3; after addition of PBO, BABA and PBO+BABA.
Figure 12:
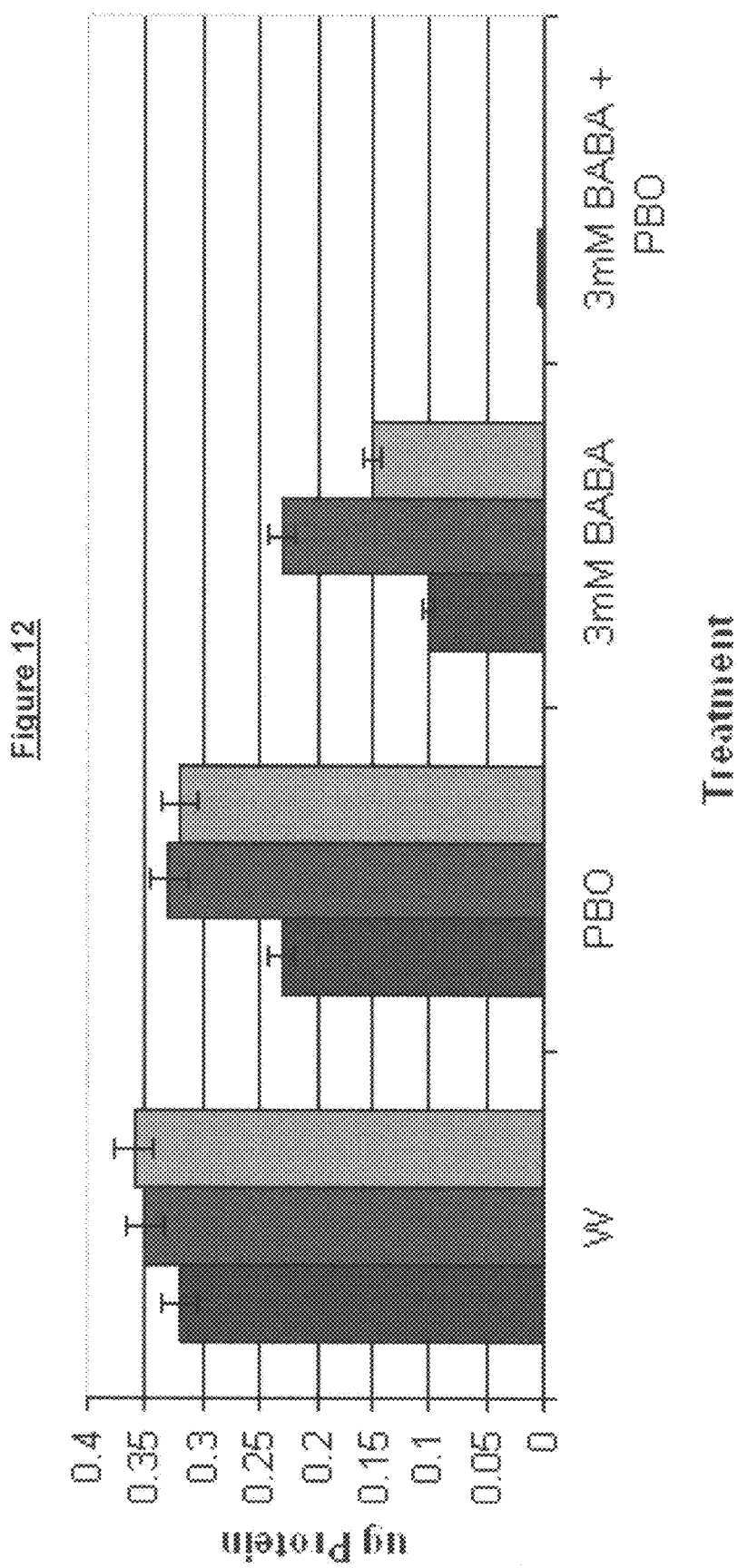
FIG. 12: Total amount of *B. tabaci* pupae protein (µg) collected from tomato plants after ~7 days in the bioassay with five tomato plants and 3 adult apterous aphid added to each plant, results for weeks 1 to 3; after addition of PBO, BABA and PBO+BABA.
Figure 13:
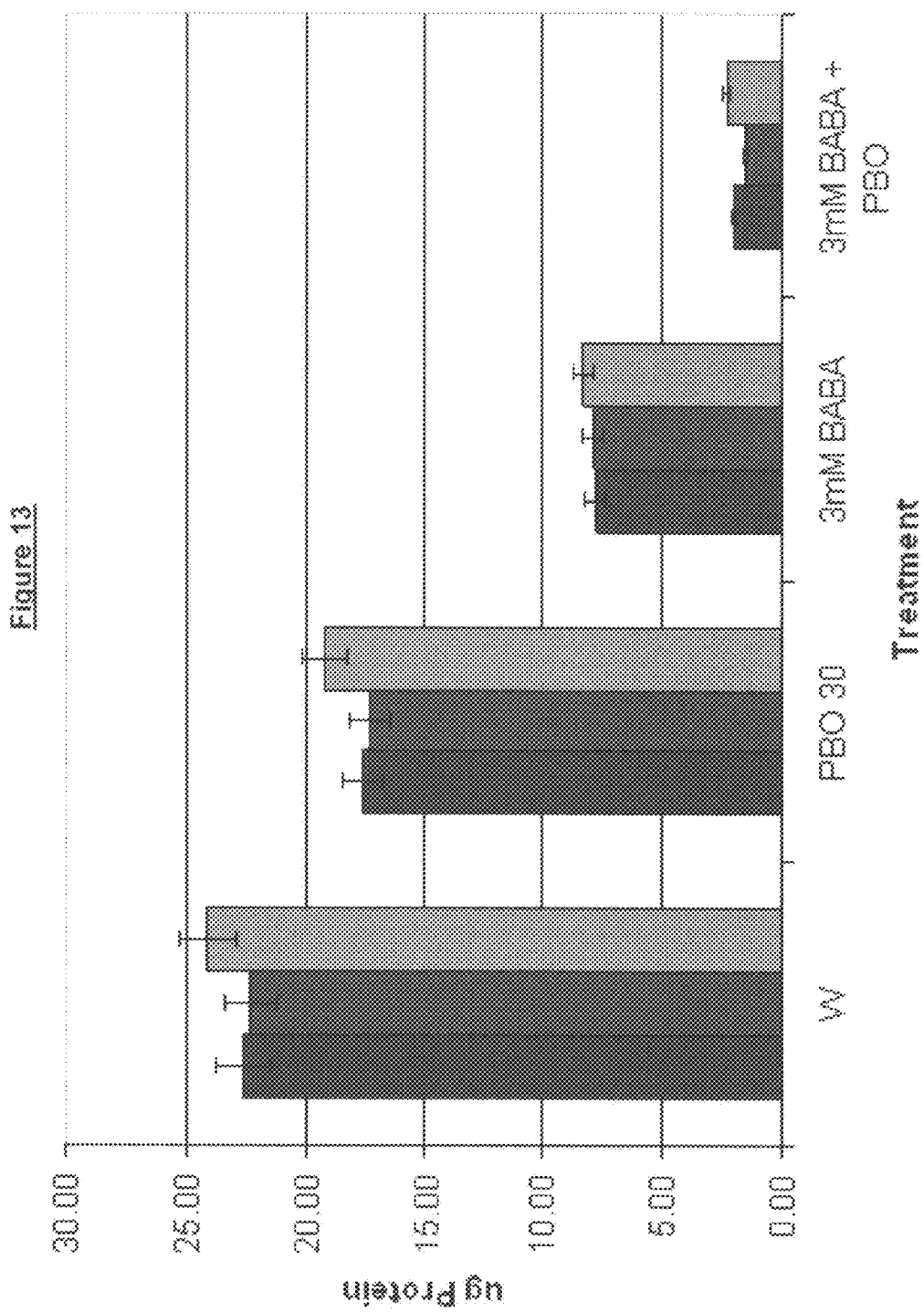
FIG. 13: Total amount of *Myzus persicae* protein (µg) collected from potato plants after 7 days in the bioassay with five potato plants and 3 adult apterous aphid added to each plant, results for weeks 1 to 3; after addition of PBO, BABA and PBO+BABA.
Figure 14:
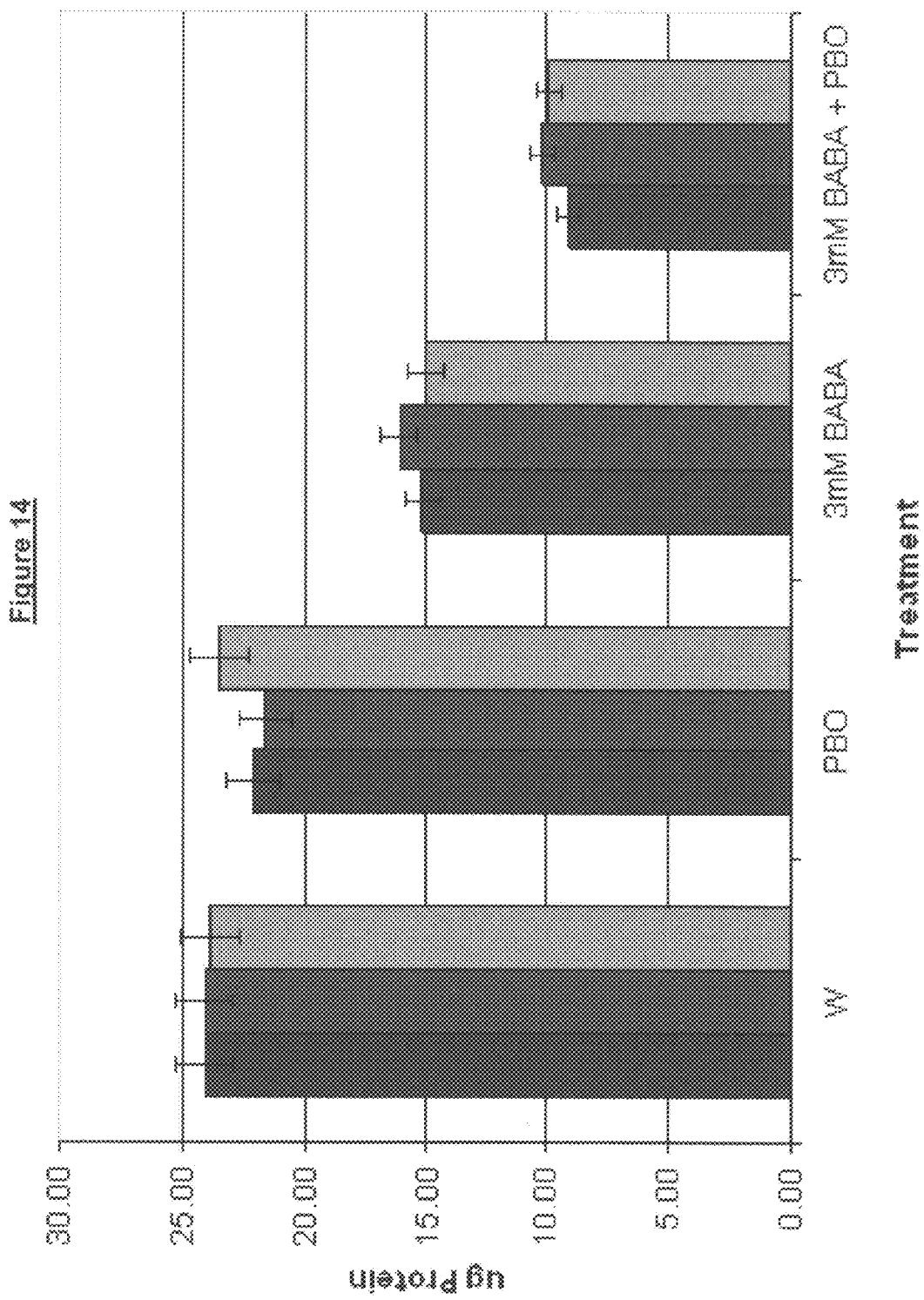
FIG. 14: Total amount of *Myzus persicae* protein (µg) collected from pepper plants after 7 days in the bioassay with five pepper plants and 3 adult apterous aphid added to each plant, results for weeks 1 to 3; after addition of PBO, BABA and PBO+BABA.
Figure 15:
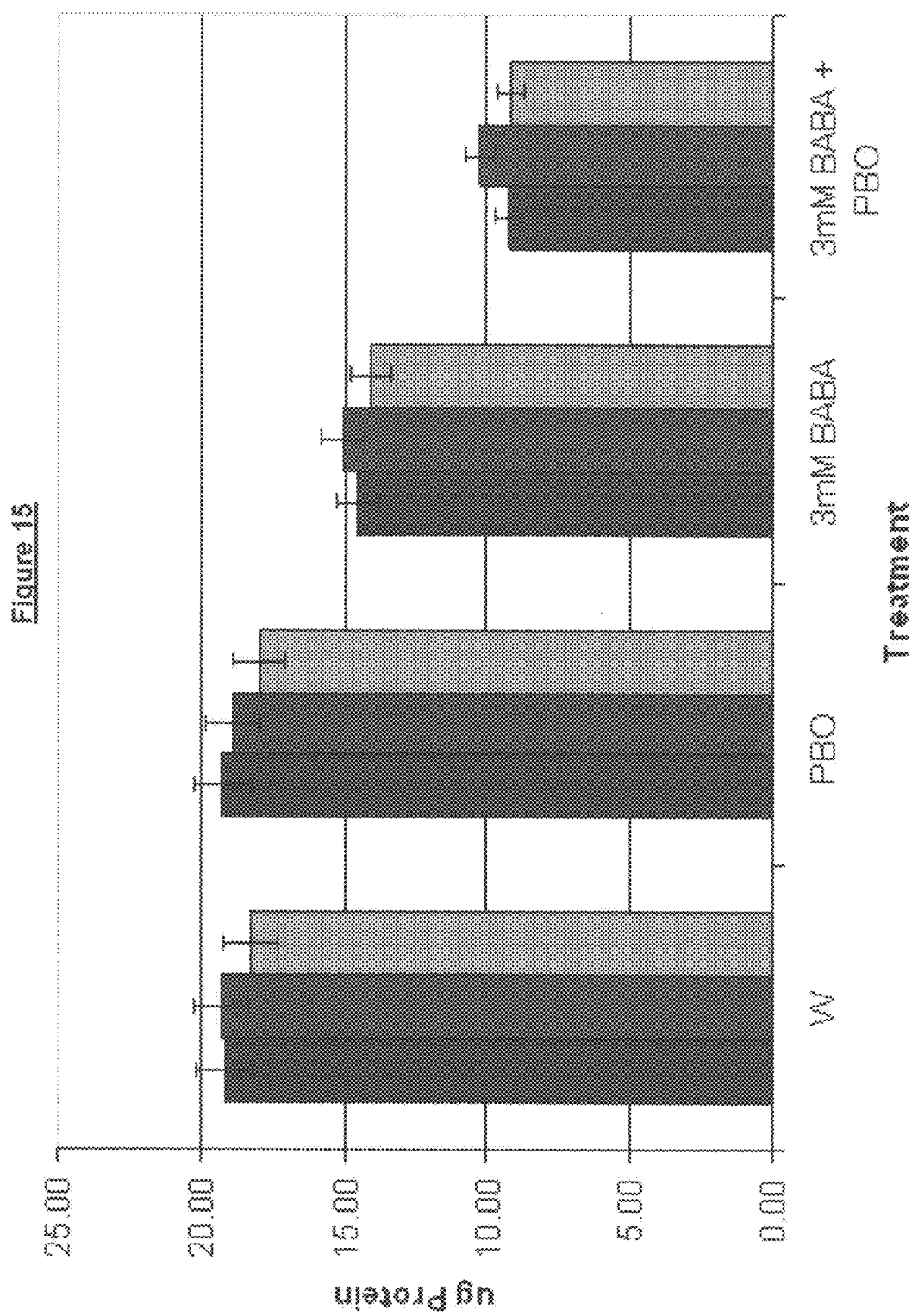
FIG. 15: Total amount of *Myzus persicae* protein (µg) collected from black mustard plants after 7 days in the bioassay with five black mustard plants and 3 adult apterous aphid added to each plant, results for weeks 1 to 3; after addition of PBO, BABA and PBO+BABA.

These results, which are depicted graphically in FIG. 10, show that propyl gallate significantly ($p<0.05$) improves the efficacy of microencapsulated cis-Jasmone on *A. gossypii*.

Comparison of these results with experiments conducted on *M. persicae* on pepper plant show that the synergist propyl gallate potentiates microencapsulated cis-Jasmone at least as well as PBO.

3.11. Effects of BABA and PBO on *M. persicae* and Whitefly Nymphs (μg) Collected from Plants after ~5 days Adult aphids were added to cotton, tomatoes, potatoes, pepper and black mustard plants and the plants treated with BABA and/or PBO as described above.

Tables 11 to 15 show the effect of BABA and/or PBO on cotton, tomatoes, potatoes, pepper and black mustard, respectively.

In these tables the abbreviations are as follows:

BABA (concentration given)+PBO=BABA+Propyl gallate/emulsified PBO

BABA=[BABA] (concentration given)

PBO=emulsified PBO.

Propyl gallate=propyl gallate (99%) powder form (dissolved in 500 μl DMSO then mixed with 100 ml deionised water)

W=deionised water.

These results are depicted graphically in FIGS. 11 to 15.

In all cases, reductions in protein content were observed when the BABA+/−PBO treatments were applied. However the effect of BABA+PBO was greater than the additive effects of BABA and PBO individually.

The development of insecticide resistance in a wide range of important insect pest species poses a serious challenge to effective crop protection, creating an urgent need for alternative control strategies. A new integrated crop management (ICM) strategy is described above which involves a unique approach, targeting specific defensive processes in both plants and insects. Inhibitors of metabolic enzyme systems (synergists) may increase the potency of insecticides. If such synergists are allowed sufficient time to inhibit these enzymes fully (temporal synergism), then the sensitivity of insect pests to pesticides may be increased by several orders of magnitude. Since plant activator-primed plants have an enhanced ability to produce defensive xenobiotics, and temporal synergism leaves the insect defenceless, a combined approach has the potential to enhance the potency of plant activators as well as insecticides. Indeed, the use of temporal synergism in conjunction with plant activator priming as described herein may result in low survival without the use of any pesticides.

TABLE 1a

| Spray | Components |
|---|---|
| Deionised Water | 100 ml deionised water |
| Blank Formulation | 0.1 ml Ethylan BV (EBV), 100 ml deionised water |
| Acetone | 100 μl Acetone, 100 ml deionised water |
| PBO Technical (97%) | 100 μl PBO Ultra, 100 ml deionised water + acetone |
| PBO E | 330 μl PBO E, 100 ml deionised water |
| cis-jasmone | 0.1 ml EBV, 100 ml deionised water, 25 μl of cis-jasmone (equivalent to 50 g ai/ha) |
| cis-jasmone + EBV PBO T + acetone | 100 μl PBO Ultra, 0.1 ml EBV, 100 ml deionised water, 25 μl of cis-jasmone (equivalent to 50 g ai/ha) + acetone |
| cis-jasmone + PBO | 330 μl PBO E, 100 ml deionised water, 25 μl of cis-jasmone (equivalent to 50 g ai/ha) |

TABLE 1b

| Spray | Components |
|---|---|
| Deionised Water | 100 ml deionised water |
| PBO E (30%) | 330 μl PBO E, 100 ml deionised water sprayed |
| BABA | [BABA] in 1000 ml deionised water applied as a root drench 25 ml/100 ml per plant |
| BABA + PBO E | [BABA] in 1000 ml deionised water applied as a root drench 25 ml/100 ml per plant 330 μl PBO E, 100 ml deionised water sprayed (0.1%) |
| BABA + Propyl gallate | [BABA] in 1000 ml deionised water applied as a root drench 25 ml/100 ml per plant 0.1% Propyl gallate in 100 ml deionised water sprayed |

TABLE 2

| Week | Treatment | μg (Av) Total Protein |
|---|---|---|
| 1 | ALL | 0.024 |
| 1 | CJ | 0.109 |
| 1 | PBO | 0.165 |
| 1 | W | 0.239 |
| 2 | ALL | 0.013 |
| 2 | CJ | 0.102 |
| 2 | PBO | 0.169 |
| 2 | W | 0.241 |
| 3 | ALL | 0.023 |
| 3 | CJ | 0.100 |
| 3 | PBO | 0.134 |
| 3 | W | 0.208 |

TABLE 3

| Week | Treatment | μg (Av) Total Protein |
|---|---|---|
| 1 | ALL | 13.56 |
| 1 | CJ | 13.82 |
| 1 | PBO | 14.72 |
| 1 | W | 14.1 |
| 2 | ALL | 13.5 |
| 2 | CJ | 13.8 |
| 2 | PBO | 14.2 |
| 2 | W | 14.2 |
| 3 | ALL | 13.46 |
| 3 | CJ | 13.9 |
| 3 | PBO | 14.3 |
| 3 | W | 14.25 |

TABLE 4

| Week | Treatment | μg (Av) Total Protein |
|---|---|---|
| 1 | W | 12.49 |
| 1 | Acetone | 16.20 |
| 1 | EBV | 17.55 |
| 1 | PBO + Acetone | 12.23 |
| 1 | PBO | 13.64 |
| 1 | CJ + EBV | 11.00 |
| 1 | CJ + EBV + PBO T + Acetone | 9.00 |
| 1 | CJ + PBO | 6.00 |
| 2 | W | 10.20 |
| 2 | Acetone | 12.20 |
| 2 | EBV | 10.26 |
| 2 | PBO + Acetone | 12.30 |
| 2 | PBO | 8.50 |
| 2 | CJ + EBV | 3.27 |
| 2 | CJ + EBV + PBO T + Acetone | 3.22 |
| 2 | CJ + PBO | 3.10 |
| 3 | W | 10.20 |
| 3 | Acetone | 11.30 |
| 3 | EBV | 15.50 |
| 3 | PBO + Acetone | 10.30 |
| 3 | PBO | 10.01 |
| 3 | CJ + EBV | 8.80 |
| 3 | CJ + EBV + PBO T + Acetone | 8.70 |
| 3 | CJ + PBO | 5.35 |

TABLE 5

| Week | Treatment | μg (Av) Total Protein |
|---|---|---|
| 1 | W | 22.50 |
| 1 | Acetone | 26.47 |
| 1 | EBV | 22.90 |
| 1 | PBO T + Acetone | 22.30 |
| 1 | PBO | 23.60 |
| 1 | CJ + EBV | 11.00 |
| 1 | CJ + EBV + PBO T + Acetone | 6.16 |
| 1 | CJ + PBO | 8.89 |
| 2 | W | 17.21 |
| 2 | Acetone | 20.20 |
| 2 | EBV | 15.47 |
| 2 | PBO T + Acetone | 16.50 |
| 2 | PBO | 17.29 |
| 2 | CJ + EBV | 11.99 |
| 2 | CJ + EBV + PBO T + Acetone | 11.80 |
| 2 | CJ + PBO | 10.25 |
| 3 | W | 22.50 |
| 3 | Acetone | 26.47 |
| 3 | EBV | 22.90 |
| 3 | PBO T + Acetone | 22.30 |
| 3 | PBO | 23.60 |
| 3 | CJ + EBV | 11.00 |
| 3 | CJ + EBV + PBO T + Acetone | 6.16 |
| 3 | CJ + PBO | 8.89 |

TABLE 6

| Week | Treatment | μg (Av) Total Protein |
|---|---|---|
| 1 | Water | 35.86 |
| 1 | Acetone | 33.61 |
| 1 | EBV | 32.62 |
| 1 | PBO + Acetone | 37.68 |
| 1 | PBO | 38.91 |
| 1 | CJ + EBV | 25.14 |
| 1 | CJ + EBV + PBO T + Acetone | 24.35 |
| 1 | CJ + PBO | 21.51 |
| 2 | Water | 35.1 |
| 2 | Acetone | 33.1 |
| 2 | EBV | 30.9 |
| 2 | PBO T + Acetone | 33.6 |
| 2 | PBO | 33.2 |
| 2 | CJ + EBV | 25.4 |
| 2 | CJ + EBV + PBO T + Acetone | 24.3 |
| 2 | CJ + PBO | 21.5 |
| 3 | Water | 33.2 |
| 3 | Acetone | 31.6 |
| 3 | EBV | 31.9 |
| 3 | PBO T + Acetone | 33.2 |
| 3 | PBO | 33.5 |
| 3 | CJ + EBV | 25.1 |
| 3 | CJ + EBV + PBO T + Acetone | 24.3 |
| 3 | CJ + PBO | 21.2 |

TABLE 7

| Week | Treatment | μg (Av) Total Protein |
|---|---|---|
| 1 | W | 0.517 |
| 1 | EBV | 0.407 |
| 1 | PBO | 0.28 |
| 1 | CJ + EBV | 0.1 |
| 1 | CJ + PBO | 0 |
| 2 | W | 0.52 |
| 2 | EBV | 0.43 |
| 2 | PBO | 0.28 |
| 2 | CJ + EBV | 0.2 |
| 2 | CJ + PBO | 0.001 |
| 3 | W | 0.53 |
| 3 | EBV | 0.42 |
| 3 | PBO | 0.3 |
| 3 | CJ + EBV | 0.2 |
| 3 | CJ + PBO | 0.002 |

TABLE 8

| Exp Type | Species | Treatment | Av. Total Insect Protein μg | ANOVA STATS |
|---|---|---|---|---|
| Simulator | M. persicae | d-water | 14.185 | p = 0.002 |
| On Pepper | (US1L) | PBO | 14.406 | SEM = 0.088 |
| (BellBoy) | | Cis-jasmone + EBV | 13.842 | LSD = 0.3057 |
| | | Cis-jasmone + PBO | 13.507 | DF = 6 |
| Simulator | Bemisia tabaci | d-water | 0.229 | p < 0.001 |
| On Tomato | (GUA MIX) | PBO | 0.156 | SEM = 0.009 |
| (Carousel) | | Cis-jasmone + EBV | 0.104 | LSD = 0.0230 |
| | | Cis-jasmone + PBO | 0.020 | DF = 6 |

TABLE 8-continued

| Exp Type | Species | Treatment | Av. Total Insect Protein μg | ANOVA STATS |
|---|---|---|---|---|
| Bioassay | Bemisia tabaci | d-water | 0.522 | $p < 0.001$ |
| | (GUA MIX) | PBO | 0.419 | SEM = 0.014 |
| | | EBV | 0.287 | LSD = 0.4578 |
| | | Cis-jasmone + EBV | 0.167 | DF = 8 |
| | | Cis-jasmone + PBO | 0.001 | |
| Bioassay 1 adult/plant | M. persicae (US1L) | d-water | 10.960 | $p < 0.001$ |
| | | EBV | 14.440 | SEM = 1.007 |
| | | Acetone | 13.230 | LSD = 3.053 |
| | | PBO | 10.710 | DF = 14 |
| | | PBOTech + Acetone | 11.610 | |
| | | Cis-jasmone + EBV | 7.690 | |
| | | Cis-jasmone + PBO | 4.820 | |
| | | Cis-jasmone + EBV + PBO + Acetone | 6.970 | |
| Bioassay 5 adults/plant | M. persicae (US1L) | d-water | 20.740 | $p < 0.001$ |
| | | EBV | 20.420 | SEM = 1.612 |
| | | Acetone | 24.380 | LSD = 4.889 |
| | | PBO | 21.500 | DF = 14 |
| | | PBO + Acetone | 20.370 | |
| | | Cis-jasmone + EBV | 11.330 | |
| | | Cis-jasmone + PBO | 9.340 | |
| | | Cis-jasmone + EBV + PBO + Acetone | 8.040 | |
| Bioassay 10 adults/plant | M. persicae (US1L) | d-water | 34.720 | $p < 0.001$ |
| | | EBV | 31.470 | SEM = 0.765 |
| | | Acetone | 32.770 | LSD = 1.082 |
| | | PBO | 35.200 | DF = 14 |
| | | PBO + Acetone | 34.830 | |
| | | Cis-jasmone + EBV | 25.210 | |
| | | Cis-jasmone + PBO | 21.400 | |
| | | Cis-jasmone + EBV + PBO + Acetone | 24.320 | |

TABLE 9

| Week | Treatment | Protein WF (Av) (μg) |
|---|---|---|
| 1 | W | 0.329 |
| 1 | PBO | 0.167 |
| 1 | CJ + EBV | 0.03 |
| 1 | CJ + PBO | 0.0001 |
| 2 | W | 0.26 |
| 2 | PBO | 0.16 |
| 2 | CJ + EBV | 0.06 |
| 2 | CJ + PBO | 0.0006 |
| 3 | W | 0.265 |
| 3 | PBO | 0.17 |
| 3 | MC CJ | 0.08 |
| 3 | MC CJ + PBO | 0.0001 |

TABLE 10

| Week | Treatment | Protein A (Av) (ug) |
|---|---|---|
| 1 | W | 20.1 |
| 1 | PBO | 20.05 |
| 1 | MC CJ | 9.2 |
| 1 | MC CJ + Propy-gallate | 2.15 |
| 2 | W | 16.2 |
| 2 | PBO | 15.1 |
| 2 | MC CJ | 9.9 |
| 2 | MC CJ + Propy-gallate | 3.25 |
| 3 | W | 17.3 |
| 3 | PBO | 16.3 |
| 3 | MC CJ | 10.2 |
| 3 | MC CJ + Propy-gallate | 3.15 |

TABLE 11

| Week | Treatment | Protein WF (Av) (ug) |
|---|---|---|
| 1 | W | 0.2585 |
| 1 | PBO | 0.14 |
| 1 | 3 mM BABA | 0.1 |
| 1 | 3 mM BABA + PBO | 0.001 |
| 2 | W | 0.26 |
| 2 | PBO | 0.14 |
| 2 | 3 mM BABA | 0.2 |
| 2 | 3 mM BABA + PBO | 0.0005 |
| 3 | W | 0.265 |
| 3 | PBO | 0.15 |
| 3 | 3 mM BABA | 0.2 |
| 3 | 3 mM BABA + PBO | 0.001 |

TABLE 12

| Week | Treatment | Protein WF (Av) (ug) |
|---|---|---|
| 1 | W | 0.32 |
| 1 | PBO | 0.23 |
| 1 | 3 mM BABA | 0.1 |
| 1 | 3 mM BABA + PBO | 0.005 |
| 2 | W | 0.35 |
| 2 | PBO | 0.33 |
| 2 | 3 mM BABA | 0.23 |
| 2 | 3 mM BABA + PBO | 0.001 |
| 3 | W | 0.36 |
| 3 | PBO | 0.32 |
| 3 | 3 mM BABA | 0.15 |
| 3 | 3 mM BABA + PBO | 0.0009 |

TABLE 13

| Week | Treatment | Protein A (Av) (ug) |
|---|---|---|
| 1 | W | 22.60 |
| 1 | PBO | 17.60 |
| 1 | 3 mM BABA | 7.80 |
| 1 | 3 mM BABA + PBO | 2.00 |
| 2 | W | 22.30 |
| 2 | PBO | 22.30 |
| 2 | 3 mM BABA | 7.90 |
| 2 | 3 mM BABA + PBO | 1.50 |
| 3 | W | 24.10 |
| 3 | PBO | 19.20 |
| 3 | 3 mM BABA | 8.30 |
| 3 | 3 mM BABA + PBO | 2.30 |

TABLE 14

| Week | Treatment | Protein A (Av) (ug) |
|---|---|---|
| 1 | W | 24.10 |
| 1 | PBO | 22.10 |
| 1 | 3 mM BABA | 15.10 |
| 1 | 3 mM BABA + PBO | 9.10 |
| 2 | W | 24.10 |
| 2 | PBO | 21.60 |
| 2 | 3 mM BABA | 16.10 |
| 2 | 3 mM BABA + PBO | 10.20 |
| 3 | W | 23.90 |
| 3 | PBO | 23.50 |
| 3 | 3 mM BABA | 15.00 |
| 3 | 3 mM BABA + PBO | 9.90 |

TABLE 15

| Week | Treatment | Protein A (Av) (ug) |
|---|---|---|
| 1 | W | 19.20 |
| 1 | PBO | 19.30 |
| 1 | 3 mM BABA | 14.56 |
| 1 | 3 mM BABA + PBO | 9.23 |
| 2 | W | 19.34 |
| 2 | PBO | 18.90 |
| 2 | 3 mM BABA | 15.10 |
| 2 | 3 mM BABA + PBO | 10.24 |
| 3 | W | 18.30 |
| 3 | PBO | 18.00 |
| 3 | 3 mM BABA | 14.10 |
| 3 | 3 mM BABA + PBO | 9.15 |

REFERENCES

Bingham, G. V., Gunning, R. V. & Moores, G. D. (2007) *Pest Management Science* 63: 276-281.

Birkett, M. A.; Campbell, C. A. M.; Chamberlain, K.; Guerrieri, E.; Hick, A. J.; Martin, J. L.; Matthes, M.; Napier, J. A.; Pettersson, J.; Pickett, J. A.; Poppy, G. M.; Pow, E. M.; Pye, B. J.; Smart, L. E.; Wadhams, G. H.; Wadhams, L. J.; Woodcock, C. M. (2000) *Proc. Natl. Acad. Sci. USA*, 97(16), 9329-9334.

Bruce, T.; Pickett, J.; and Smart, L. (2003) Pesticide Outlook June 2003 96-98.

Bruce, T. J., Martin, J. L., Pickett, J. A., Pye, B. J., Smart, L. E. and Wadhams, L. J. (2003) Pest Management Science 59: 1031-1036

Chamberlain, K.; Pickett, J. A.; Woodcock, C. M. (2000) *Mol Plant Pathol* 1:67-72

Devine, G. & Denholm, I. (1998) In Piperonyl Butoxide, The Insecticide Synergist. Ed. Glynne Jones, D. pp 227-238.

Dewhirst, S. (2007) PhD thesis, Imperial College, London.

Grant, D. F.; Bender, D. M.; Hammock, B. D. *Insect Biochem.* 1989, 19, 741-751.

Hodge, S, Thompson, G A & Powell, G (2005). *Bull. Ent Res* 95: 449-455.

Hodge, S, Pope, T W, Holaschke, M & Powell, G (2006) (in press).

Moores, G. D., Bingham, G. and Gunning, R. V. (2005) *Outlooks on Pest Management* 16: 7-9.

Pickett, J. A.; Poppy, G. M. (2001) *TRENDS Plants Sci* 6:137-139

Young, S. J., Gunning, R. V. & Moores, G. D. (2005) *Pest Management Science* 61: 397-401.

Young, S. J., Gunning, R. V. & Moores, G D (2006) *Pest Management Science* 62: 114-119.

What is claimed:

1. A method of controlling plant pests which comprises; contacting a plant with a composition including one or more plant synergists and one or more plant activators wherein the one or more plant synergists is a member selected from the group consisting of piperonyl butoxide (PBO), sesamex, sesamolin, sesamin, sulfoxide, tropital, propyl isome, MGK 264, propynyl phosphonate, N-isobutylundecylenamide, octachlorodipropyl ether, propyl gallate, a methylenedioxyphenyl (MDP) compound, and combinations,
wherein the one or more plant activators is a member selected from the group consisting of cis-jasmone, methyl jasmonate, β-amino butyric acid and Ocimene,
wherein the composition does not include an essential plant oil comprising a monocyclic, carbocyclic ring structure having six-members and substituted by at least one oxygenated or hydroxyl functional moiety.

2. A method according to claim 1 wherein the plant is not contacted with essential plant oils.

3. A method according to claim 1 wherein the composition consists essentially of one or more plant synergists and one or more plant activators.

4. A method according to claim 1 wherein the plant is additionally contacted with a pesticide or a penetration promoting agent.

5. The method according to claim 1 wherein one or more plant synergists and one or more plant activators are non-toxic compounds.

6. The method according to claim 2 wherein the one or more plant synergists inhibit, suppress, or otherwise diminish the activity of a plant pest's mechanisms for overcoming, deactivating or avoiding susceptibility to plant xenobiotics or pesticides.

7. The method according to claim 1 wherein one or more plant synergists are applied before, after or concurrent with treatment of the plant with the plant activator.

8. The method according to claim 1 wherein the one or more plant synergists is a member selected from the group consisting of an MDP compounds, propyl gallate and combinations thereof.

9. The method according to claim 1 wherein the one or more plant synergists are PBO or propyl gallate or both.

10. The method according to claim 1 wherein the one or more plant activators is a compound which induces said plant to produce or over-produce xenobiotics or which attracts plant pest parasitoids to the plant.

11. The method according to claim 1 which comprises contacting a plant with PBO and cis-jasmone.

12. The method according to claim 1 which comprises contacting said plant first with PBO and then with cis-jasmone.

13. The method according to claim 1 wherein said activator is administered in combination with an agent which promotes penetration of said activator into said plant.

14. The method according to claim 13 wherein the penetration promoting agent is nonylphenol ethoxylate.

15. A composition for control of plant pests comprising one or more plant synergists and one or more plant activators;
wherein the one or more plant synergists is a member selected from the group consisting of piperonyl butoxide (PBO), sesamex, sesamolin, sesamin, sulfoxide, tropital, propyl isome, MGK 264, propynyl phosphonate, N-isobutylundecylenamide, octachlorodipropyl ether, propyl gallate, a methylenedioxyphenyl (MDP) compound, and combinations,
wherein the one or more plant activators is a member selected from the group consisting of cis-jasmone, methyl jasmonate, β-amino butyric acid and Ocimene,
wherein the composition does not include an essential plant oil comprising a monocyclic, carbocyclic ring structure having six-members and substituted by at least one oxygenated or hydroxyl functional moiety.

16. The composition according to claim 15 which provides for temporal control over release of said plant synergist, control over release of said plant activator, or control over release of both said plant synergist and said plant activator.

17. The composition according to claim 16 wherein the one or more plant synergists or the one or more plant activators are encapsulated.

18. The composition according to claim 17 wherein the release of the one or more plant synergists begins at a time from several hours prior to release of the one or more plant activators to several hours following release of the one or more plant activators.

19. The composition according to claim 16 wherein the release of said synergist ends at a time from several hours prior to release of said activator to several hours following release of said activator.

20. The composition according to claim 17 which comprises an encapsulant selected from the group consisting of cyclodextrins, yeast, gum acacia, polyurea, and combinations thereof for the delayed release of either or both of the synergist or plant activator, either simultaneously or separately.

21. A composition for control of plant pests comprising PBO and cis-jasmone, and which optionally comprises nonylphenol ethoxylate,
wherein the composition does not include an essential plant oil comprising a monocyclic, carbocyclic ring structure having six-members and substituted by at least one oxygenated or hydroxyl functional moiety.

22. The composition according to claim 16 wherein said plant activator is released over a short time frame of minutes up to a period of release over several days.

* * * * *